(12) United States Patent
Johansen et al.

(10) Patent No.: US 8,149,411 B2
(45) Date of Patent: Apr. 3, 2012

(54) SENSOR UNIT FOR A SURFACE PLASMON RESONANCE (SPR) UNIT

(75) Inventors: Knut Johansen, Linköping (SE); Mats Rånby, Vreta Kloster (SE)

(73) Assignee: Knut Johansen, Linkoping (SE)

( * ) Notice: Subject to any disclaimer, the term of this patent is extended or adjusted under 35 U.S.C. 154(b) by 409 days.

(21) Appl. No.: 12/447,825

(22) PCT Filed: Oct. 29, 2007

(86) PCT No.: PCT/SE2007/000950
§ 371 (c)(1),
(2), (4) Date: Apr. 29, 2009

(87) PCT Pub. No.: WO2008/054282
PCT Pub. Date: May 8, 2008

(65) Prior Publication Data
US 2010/0103421 A1 Apr. 29, 2010

(30) Foreign Application Priority Data
Oct. 31, 2006 (SE) ........................... 0602286

(51) Int. Cl.
G01N 21/55 (2006.01)
G01J 4/00 (2006.01)
(52) U.S. Cl. .................. 356/445; 356/244; 356/367
(58) Field of Classification Search .......... 356/445–448, 356/244, 246, 367; 436/514, 527; 435/287.2, 435/288.7; 422/82.05, 82.11
See application file for complete search history.

(56) References Cited

U.S. PATENT DOCUMENTS

| 5,257,093 A * | 10/1993 | Mager et al. ............... 356/625 |
| 6,480,282 B1 | 11/2002 | Chinowsky et al. |
| 6,752,963 B2 * | 6/2004 | Dickopf et al. ........... 422/82.09 |
| 7,501,649 B2 * | 3/2009 | Naya et al. ...................... 257/9 |

(Continued)

FOREIGN PATENT DOCUMENTS
EP 1186881 A1 3/2002
(Continued)

OTHER PUBLICATIONS

J. Rooney, et al., "Designing a curved surface SPR device," Sensor and Actuators B (Chemical), vol. 114, Elsevier, Switzerland, 2006, pp. 804-811.

(Continued)

Primary Examiner — Sang Nguyen
(74) Attorney, Agent, or Firm — Lucas & Mercanti LLP; Robert P. Michal

(57) ABSTRACT

The invention relates to a sensor unit for a Surface Plasmon Resonance (SPR) unit, comprising a transparent sensor structure forming at least one wall of a cavity, the wall being defined by a concave inner surface and a convex outer surface The inner surface is provided with a layer of a conductive material capable of supporting a surface plasmon. In the cavity there is provided a flow structure in said cavity so as to form at least one compartment for sample between the flow structure and the inner wall of the cavity. Also, a method for the detection of events at a surface by utilizing surface plasmon resonance is provided. It comprises placing a sample with an analyte of interest in a sensor unit as claimed in claim 1, and measuring the reflectance from said sensor unit at a single or plurality of angle/angles.

13 Claims, 39 Drawing Sheets

U.S. PATENT DOCUMENTS

| | | | |
|---|---|---|---|
| 7,826,042 B2 * | 11/2010 | Yamamichi et al. | 356/72 |
| 7,884,940 B2 * | 2/2011 | Mirsky et al. | 356/445 |
| 2003/0132406 A1 * | 7/2003 | Waldhausl et al. | 250/574 |
| 2007/0014505 A1 * | 1/2007 | Hosomi et al. | 385/12 |
| 2007/0106954 A1 * | 5/2007 | Porter | 715/781 |
| 2007/0153284 A1 * | 7/2007 | Glazier et al. | 356/445 |
| 2007/0273884 A1 * | 11/2007 | Matsushita et al. | 356/445 |
| 2009/0103091 A1 * | 4/2009 | Jones et al. | 356/342 |

FOREIGN PATENT DOCUMENTS

| | | |
|---|---|---|
| JP | 2003-075333 A | 3/2003 |
| JP | 2003-294615 A | 10/2003 |

OTHER PUBLICATIONS

PCT International Search Report of corresponding International Application No. PCT/SE2007/000950, dated Feb. 7, 2008 (4 pages).

PCT Written Opinion of International Seaching Authority for corresponding International Application No. PCT/SE2007/000950, dated Feb. 7, 2008 (4 pages).

Chinowsky, T.M. and Yee, S.S., "Surface Plasmon Resonance Sensing in Capillaries," Electronics Letters, 1999. vol. 35, No. 19, p. 1659-1661.

* cited by examiner ism and substrate to obtain good optical coupling. The material can either be an opto-gel [8] or a refractive index matching fluid. The use of an opto-gel has the disadvantage of wear, optical imperfection and high cost. If a refractive index matching fluid is used, a circumstantial procedure of application and cleaning is needed, besides the extra cost. There are other configurations, e.g. a prism with evaporated metal film [9] and SPR-light-pipe [10], that do not need an optical coupling medium. Yet another configuration that doesn't need to use an optical coupling medium, is a capillary [11]. In another configuration, the fiber optic SPR [12-14], on can refrain from using an optical coupling medium, but for the case of an exchangeable probe, a coupling medium is needed.

SENSOR UNIT FOR A SURFACE PLASMON RESONANCE (SPR) UNIT

This application is a U.S. National Phase Application under 35 USC 371 of International Application PCT/SE2007/000950 filed Oct. 29, 2007, which claims priority from Swedish Application No. SE 0602286-7 filed Oct. 31, 2007, the entire disclosure of each of which is incorporated herein by reference.

FIELD OF THE INVENTION

The present invention relates to a method, apparatus and device for optical surface analysis of a plurality of sample areas on a curved sensor unit using surface plasmon resonance. The invention is particularly concerned with a rotational symmetric container or tube or a device using an angular part of a rotational symmetric container, using surface plasmon resonance (SPR), suitable for use in biological, biochemical, chemical and physical analyzing, as well as gas sensing, where the container or tube may be fixed or movable, e.g. rotating or oscillating.

BACKGROUND OF THE INVENTION

There is an interest in surface sensitive techniques for analyzing the amount of molecules and larger substances, their chemical and physical properties, and their interactions with other molecules or materials. Properties that are of interest are e.g. the concentration of molecules in a solution or gas, the surface concentration of molecules on a sensor surface, the reaction kinetics of interacting substances, the affinity of the substances, allosteric effects or epitope mappings. Examples of interacting substances are antigen-antibody, protein-protein, receptor-ligand, DNA-DNA, DNA-RNA, protein-DNA, peptides-proteins, carbohydrates-proteins, glycoproteins-proteins, etc. There is also an interest in measuring the concentration of different gases or liquids, which can be performed by measuring the change in the optical density of a sensing material, e.g. polymer films, that are affected by some substance, e.g. fluid or gas [1, 2]. Change of conformation or formation of new materials on a surface, e.g. blood coagulation and fibrinolysis are also of large interest [3] [4] [5] [6]. There are many techniques that are suitable for these tasks, e.g. surface plasmon resonance (SPR), resonant mirror, grating couplers, interferometers, surface acoustic wave (SAW), Quartz Crystal Microbalance (QCM) etc. SPR is a popular technique, which have been proven to be both sensitive and reliable.

Areas of application are e.g. measurement of concentration of substances in biological research, biochemistry research, chemical research, clinical diagnosis, food diagnostics, environmental measurements, etc. Kinetic measurements can be used to determine rate constants as ($k_{on}$) and ($k_{off}$). Affinity measurements can be used to determine equilibrium association ($K_A$) or dissociation ($K_D$) constant as well as avidity.

SPR is a well-known phenomenon that is a bound electromagnetic wave, due to oscillations of electrons at the interface between a plasma and a dielectricum. The surface plasmon can only exist at an interface between the plasma (e.g. a metal) and the dielectricum. A change in the optical constants of the dielectricum will change the propagation constant of the surface plasmon. The surface plasmon can be excited by light if the propagation constant of the light parallel to the interface is equal to, or close to, the propagation constant of the surface plasmon. Normally, the Kretschmann configuration [7] is used where a thin metallic film is applied on a prism, having a higher refractive index than the measured sample. This is also denoted backside illumination, because no light is propagating in the sample medium. The surface plasmon is then evanescently excited under total internal reflection, i.e. at an incident angle, normal to the surface, larger than the critical angle. At a certain incident angle, the component of the wave vector parallel to the surface meets the real part of the complex wave vector for a surface plasmon, and hence the light will couple into the surface plasmon and propagate at the interface between the plasma and the dielectricum. The surface plasmon will reradiate into the prism, and for a certain thickness of the plasma a destructive interference will occur, leading to zero or close to zero intensity of the reflected light. For a smooth surface of the plasma, coupled light will be absorbed in the plasma and generate heat. When molecules bind close to the interface (within the probe depth of the surface plasmon) the interaction can be detected by a shift in the resonance condition of the surface plasmon. This can be detected as a shift in a reflected light intensity. This is also the case when a layer changes its density due to conformal changes or external interference.

The most common way to design an SPR apparatus is to use a prism (triangular, hemispherical or an arbitrary shape) and apply to the prism a separate planar substrate carrying the SPR-metal. In this case it is necessary to use a refractive index matching material between the pr The surface plasmon resonance (SPR) phenomenon was already described in 1959 [15] and SPR apparatuses for thin adlayer analysis have been thoroughly described since 1968 [16, 17]. SPR setups for biosensing were used for the first time in 1982 [1] and for imaging applications in 1987 [18, 19]. With imaging SPR, also denoted SPR microscopy, new applications arise, e.g., label free—real time—multi spot biochemical analyses [20, 21], which can increase the throughput tremendously. The pioneering work on imaging SPR was undertaken by Knoll et al., who investigated surfaces patterned with Langmuir-Blodgett films [22, 23]. They also investigated the physical aspects of the technique, including lateral resolution [24], and proposed different setups, e.g. the rotating grating coupler [25].

Most SPR setups utilize a separate planar sensing substrate, refractive index matching layer, and a coupling element, e.g. a prism. Using a planar sensor surface with multiple sensor areas arranged in a two-dimensional way, means that there are a couple of somewhat cumbersome (and expensive) ways to read the optical output from the surface plasmon resonance device. In principle, there are two methods to perform a readout, by mechanically scan the sensor substrate, or the use of imaging optics. Not only is the read out complex, but the distribution of samples for investigation is often very complex, with use of valves and channels or expensive autosamplers.

However, there are approaches that do not use planar substrates. Chinowsky et al. are using an approach [11], where a capillary tube is used, U.S. Pat. No. 6,480,282. The tube wall itself is the then the coupling medium, and no index matching fluid is necessary. The capillary is useful for multi sensor configuration, where the other techniques can be critical angle detection, fluorescence, chemiluminiscence, adsorption or Raman scattering. It can, with difficulties be used as an axial multispot sensor, and with severe difficulties may be with some sensors spots radially separated. However, this approach has several disadvantages. It is very difficult to cover the inside of the capillary tube with a metal of precise thickness, due to the small diameter and long length. Capillary tubes are not normally high precision optics, which will distort optical images. The capillary device is suitable for one or a few sensing spots, and the small diameter means that there will be difficulties to manufacture device with many sensors spots. The capillary device has typically a relatively large diameter, e.g. 400 µm, compared to a thin flowcell, e.g. 10 µm, making the capillary tube inefficient regarding small sample volumes, and mass transport.

Another structure similar to the capillary device is proposed by Nakaso Nobutaka, Japan patent JP2003-294616. It uses a curved cavity, with a diameter of typically 20 µm e.g. a cylinder, or part of a sphere, which is formed in a transparent block. The block has a typical dimension of 2×2 mm, and is typically cut from a glass wafer of thickness 0.2 mm. The different blocks, having different recognition molecules, can be stacked. The surface plasmon is exited radial inside the cavity.

Yet another structure that uses a curved sensor surface is proposed by Atsushi et al. Japan Patent JP2003-075333. This device uses curved cavities for recognition sites, preferably many cavities are used for a multi spot sensor. The cavity can be cylindrical, spherical or an arbitrary curvature, and the surface plasmon is exited radially, as described by Chinowsky. However, the outer surface, which is hit by the incident light, is planar. The proposed cavity is not intended for multiple sensor areas.

Using a small radius at the surface plasmon carrying surface, will not only lead to mismatch between wavevector for surface plasmon and incident light, but also leads to difficulties to obtain small light beams and smooth reflectance curves.

A SPR-setup utilizing a convex curved SPR-supporting surface is described by Rooney et al., Sensors and Actuators B, 26 Apr. 2006. There is also described a SPR-setup consisting of a tubular cup, where a SPR-supporting layer is present on the planar bottom, EP 1186881, Haya et al., 2002 (Fuji Photo Film Co).

SUMMARY OF THE INVENTION

In view of the shortcomings of prior art devices, the object of the invention is to provide an improved SPR device enabling e.g. analysis of multiple samples in a simple manner, and also which is easy and inexpensive to manufacture.

This object is achieved with a device as claimed in claim 1, by a sensor unit comprising a transparent sensor structure forming at least one wall of a cavity, the wall being defined by a concave inner surface and a convex outer surface; wherein the inner surface is provided with a layer of a conductive material capable of supporting a surface plasmon; a flow structure in said cavity so as to form at least one compartment for sample between the flow structure and the inner wall of the cavity. The flow structure is suitably provided as an insert fitting in the cavity, the insert being configured and structured so as to provide the required channels, compartments or other spaces necessary to accommodate a sample. The configuration of the inset makes it also ideal for precise temperature control of the sample.

Thus, a new configuration of a surface plasmon resonance set up is presented. A sensor unit device with convex curved outer surface and concave inner surface, in one or two dimensions is used (e.g. cylinder or hemisphere). The inner surface is, at least partly, covered with a conductive layer, having the possibility to carry a surface plasmon. The device is a development from the planar structure having the possibility to incorporate multiple recognition sites in one or two dimensions. The curvatures of both the outer and inner surfaces means that the structure itself acts as an optical device eliminating expensive optics for light sources and detectors, e.g. a collimated incident beam will be transformed to a multi angle beam incorporating incident angles of interest by the curved outer and inner surfaces, and further spread to a detector, without the use of other optics. The use of macroscopic dimensions like in the conventional planar configuration, means that a flow structure is easily incorporated close to or in contact with the inner surface. The flow structure can in its simplest form be a wall close to the inner surface, incorporated in the optical structure. Such a wall can decrease sample volumes, without decreasing the advantage of macroscopic size of the sensor unit. With an insert, versatile fluidistics can be formed, both for immobilization of recognition molecules and samples. The curvature makes the device ideal for rotation, whereas different rows of recognition sites can be addressed both optically and by the flow cells in a single operation, eliminating expensive fluidistics. Especially, it is ideal as a diagnostic revolver, where one or more analytes are measured by one or more sensor sports axially, and different samples are analyzed by rotating the device, using new sensor spots, for the same or different analytes. The surface plasmon is exited radially, and one embodiment is a closed structure, another is an open one, where an angular part of the structure is missing, e.g. a tube which is axially cut in half.

In one embodiment a rotational symmetry makes the device ideal for monitoring of substances or the formation of new substances close to the wall. The shape of the device makes it ideal for multi-spot and large area detection. The shape makes it easy to scan the whole inner surface of the device by either rotating the device or by rotating the light source and detector. A rotational symmetry and macroscopic dimensions are ideal for an insert containing a flow system with sample distribution.

Use of macroscopic dimensions leads to simpler optics where beam widths from commercial components can be used with optical output that generates surface plasmon resonance angles of interest, e.g. for effective refractive indices from e.g. 1.33 to 1.45. Yet another advantage due to the relatively large radius if the inner surface is a little bent surface plasmon wave, and hence unwanted optical effects are avoided, e.g. interferences and bad coupling to the surface plasmon.

Not only is this new configuration perfect for measurements using surface plasmon resonance, it also leads to a much simpler instrument than is previously standard. The absence of a refractive index matching substance leads to both lower cost, less maintenance and simpler handling. The physical dimensions of the device mean that is easy to manufacture with high precision and at a low cost. Because the device can easily be sealed, it is also perfect for hazardous substances.

The invention can easily be fitted with an effective temperature control. A symmetric configuration of a SPR-tube/ vial will reduce temperature gradients, and therefore it is suitable for accurate temperature control and high precision measurements.

The invention can be used for biosensing, e.g., for monitoring of chemical and biological reactions in real time with label-free molecules. A set-up with a collimated light source in a new configuration with gold as the supporting metal is described, both theoretically and experimentally. Simulations of the sensor response based on independently recorded optical (ellipsometric) data of gold show that the proposed optical set up working as a surface sensitive differential refractometer, where the performance is equal or better than contemporary instruments.

A closed configuration of the sample area makes it ideal also for gas sensing.

The main advantages of the invention are: Simpler and cheaper instrument and consumables can be produced.

The elimination of a refractive index matching layer (as used in the Kretschmann configuration) means that the handling and change of sensors surfaces are easily performed.

A rotational or partly rotational symmetry of the sensor surface means that it can be used in conjunction with a rotating bob creating shear rates and a more effective mass transport of the analyte to the sensing surface The use of a conical bob and/or vial means that a gradient of the immobilized molecules can easily be created. Furthermore, due to different mass transport conditions, a gradient of the free analyte can also be created. These properties make it possible to perform an effective interaction analysis.

The design as a circular container means that a sample and flow handling system can be integrated inside the cavity. Even the waste can be integrated, e.g. for safety reasons.

The SPR tube, cup or vial can have the advantage of utilizing the rotational symmetric configuration, where the wall acts as a coupling medium, which increases the propagation vector parallel to the inner surface of the tube, making it possible to excite a surface plasmon. The use of the wall means that no refractive index matching medium, e.g. fluid, gel or film, is necessary, leading to a simple and cheap set up. Furthermore, the handling and change of sensor surfaces are then very simple. A rotational symmetric structure of the tube/vial, means that the tube/vial can be rotated and scanned over the whole inner surface, making it ideal for multi-spot measurements. A rotational symmetric configuration make it possible to place inserts within the vial/tube which are easily sealed.

If the SPR tube/vial is conical, a correspondingly conical insert will be self-positioned and self-tightened, by virtue of it fitting exactly in the cavity, making it an ideal structure for an integrated flow system, as will be disclosed below in detail. The system can also be made leakage proof.

It is also ideal when a bob (fixed or rotating) is used. The rotation of the bob relative the tube/vial makes it possible to monitor interactions, adlayer formations, and conformal changes at different shear rates. The SPR-vial can efficiently be used in the monitoring of polymerization and depolymerization processes [3], e.g. hemostasis.

Whereas reflectance measurements of p-polarized light is the dominating technique for SPR, the polarization state, i.e. ellipsometric measurements can be performed, using both p- and s-polarized light. Severeral ellipsometric techniques are well known for planar structures, such as null ellipsometry, off null ellipsometry, rotatating analyzer etc, which all can be used in the proposed structure.

For enhancement of the response signal, a sandwich assay can be used, where an immobilized molecule act as capturing molecule for an analyte molecule, and a third molecule is attached to the analyte either by mixing in the sample or by a further reagent step. The third molecule can be a large molecule, or have high refractive index or using both properties.

Further scope of applicability of the present invention will become apparent from the detailed description given hereinafter and the accompanying drawings which are given by way of illustration only, and thus not to be considered limiting on the present invention.

The invention is now illustrated by description of embodiments with reference to the drawings and experiments, but it should be understood that the invention is not limited to the specifically disclosed embodiments.

DETAILED DESCRIPTION OF PREFERRED EMBODIMENTS

SPR-Technique

Figure 1A:
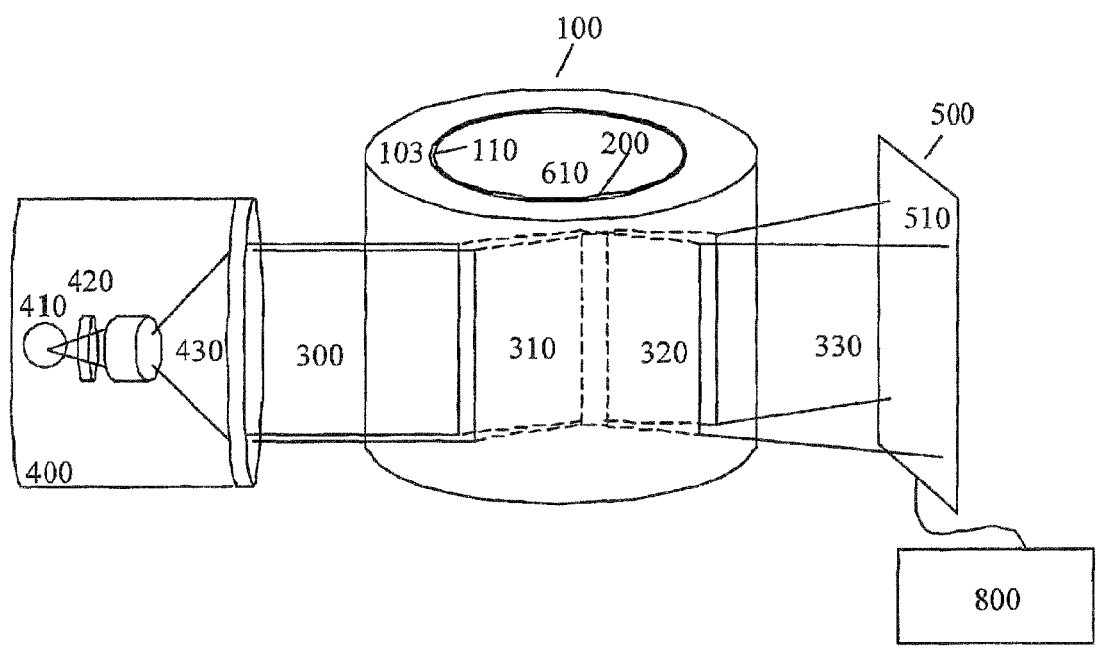
FIG. 1a shows an apparatus for surface plasmon resonance measurements with a line shaped beam (tilted view) without an imaging lens.

The surface plasmon is excited by an electromagnetic wave, in the visible region denoted light, which electrical field can be described as:

$$\overline{E} = \overline{E}_0 e^{i(\overline{k}\cdot\overline{r} - \omega t)} \quad (1)$$

where E is the varying electrical field in time and space, $E_0$ a field strength constant, k the propagation constant, r the space vector, ω the angular frequency, and t the time. The surface plasmon is excited by the electrical field component parallel to the plane of incidence, i.e. p-polarized light, also denoted transverse magnetic (TM).

The propagation constant is given by:

$$k = k_0 \cdot N = \frac{\omega}{c} N = \frac{2\pi}{\lambda} N \quad (2)$$

where $k_o$, is the free space propagation constant, N is an effective refractive index, c the speed of light in free space, and λ the wavelength in free space.

The propagation constant of a plasmon can be calculated from Maxwells Equations, and is for the semi-infinite case given by [26]:

$$k_{SP} = k_0 N_{SP} = k_0 \sqrt{\frac{\varepsilon_m(\omega) \cdot \varepsilon_a}{\varepsilon_m(\omega) + \varepsilon_a}} \quad (3)$$

where $k_{SP}$ is the (complex) surface plasmon propagation constant, $N_{SP}$ is the effective (complex) refractive index of the surface plasmon, $\varepsilon_m(\omega)$ is the frequency dependent dielectric function (complex) of the metal carrying the plasmon, and $\varepsilon_a$ is the effective dielectric function of the ambient medium (normally real, but can be frequency dependent and complex). The effective dielectrical function is monitored (weighted within the probe depth of the surface plasmon) by the surface plasmon. The function of the weighting is exponential decaying, and given by:

$$e^{-\frac{z}{\delta}} \quad (4)$$

where z is the space coordinate out from the surface, and δ is the characteristic probe depth.

The characteristic probe depth is a function of the wavelength and the polarizability of the material, and is at resonance given by:

$$\delta = \frac{\lambda}{4\pi} \cdot \frac{1}{\text{Im}\left[\frac{\varepsilon_a}{\sqrt{\varepsilon_m + \varepsilon_a}}\right]} \quad (5)$$

The surface plasmon will propagate along the interface and its intensity will decay exponentially:

$$I \propto e^{-\frac{x}{L_{SP}}} \ldots \quad (6)$$

where x is the coordinate along the interface parallel to the propagation, and $L_{SP}$, is a characteristic propagation length, which is given by:

$$L_{SP} = \frac{1}{2\text{Im}[k_{SP}]} = \frac{\lambda}{4\pi} \cdot \frac{1}{\text{Im}[N_{SP}]} = \frac{\lambda}{4\pi} \cdot \frac{1}{\text{Im}\left[\sqrt{\frac{\varepsilon_m(\omega) \cdot \varepsilon_a}{\varepsilon_m(\omega) + \varepsilon_a}}\right]} \quad (7)$$

There are in principal three different ways to measure changes in the SPR-propagation constant. First, by measuring the reflected intensity (reflectance) at a flank of the SPR-dip at a certain wavelength and incident angle. Second, by measuring the intensity of the reflected light versus the angle of the incident light (angular interrogation). Third, by measuring the intensity of reflected light for different wavelengths at a certain incident angle (wavelength interrogation).

For zero-dimensional SPR (measurement of a single spot) the intensity measurement requires only a spot (one element) detector. A one-dimensional SPR measurement (measurement of a single line) the intensity measurement requires a one-dimensional (line) detector to make an instant measurement of the position of an SPR-dip. If a two dimensional (matrix) detector is used, a two-dimensional sensor surface can be monitored. The intensity measurement has the disadvantage that only a small part of the SPR-dip is measured. This can lead to false interpretations, if, e.g. the dip is broadening or influenced by a drifting offset. If the whole dip is measured as in the angular and wavelength interrogation, these drawbacks are eliminated or at least significantly reduced.

If the angular or wavelength interrogation is used, one dimension of the sensor surface is eliminated and replaced by an SPR-dip, i.e. a two-dimensional detector can monitor a line, and a one line-detector can monitor a spot. In this case, one dimension is used for the length scale (real image) and one dimension is used for the dip (either angle or wavelength). However, if the SPR-tube/vial is rotated, a fully two-dimensional surface can be monitored by a two-dimensional detector, measuring the whole SPR-dip, and a line can be monitored by a one-dimensional detector, using this scanning technique.

The preferred detection method for the SPR-tube/vial is the angular interrogation. If a collimated (parallel) or slightly divergent or convergent light is used, the light beam will hit the outer wall of the tube/vial and refract into the inner surface at a continuum of incident angles due to the width of the beam. The total internal reflected beam will be further refracted at the outer surface, creating a divergent beam, where the SPR-dip (angular) are easily monitored by a photodetector or a photographic film. The relation between the incident angle, α, at the outer surface and the incident angle, θ, at the inner surface is given by:

$$\sin\theta = \frac{r_o \cdot n_0}{r_i \cdot n_1} \cdot \sin\alpha \quad (8)$$

where $r_o$ and $r_i$ are the radii of the outer and inner surfaces respectively, and $n_0$ is the refractive index for the ambient medium outside the device (normally air) and $n_1$ is the refractive index of the device. From equation 8 it follows that there is only a limited range of incident angles, θ, at the inner surface, depending on the values of $r_o$, $r_i$, $n_0$, and $n_1$. For the case that the refractive index of the substrate is higher than the ratio between the outer radius and inner radius, it is not possible to obtain high incident angles at the inner surface (it is assumed that the ambient is air).

If collimated light is used, the width of the beam will lead to a finite measuring spot, where the different positions on the curved surface is associated with a specific incident angle. This means that the position for resonance will change when the resonance condition is changed. The change is dependant on the ratio between the inner and outer radius, but can for most cases be neglected. Typically, for a crown glass tube with 12 mm outer diameter and 8 mm inner radius, the movement of the measuring spot is 100 μm for every degree the resonance condition is shifted. This corresponds approximately to 10 μm for 1000 μRIU, i.e. the movement is of the same order as the propagation length of the plasmon. This means that for most purposes the movement of the measuring spot is insignificant.

The presence of a curved surface on the tube means that the surface plasmon will "change direction" along the surface, which may lead to a lower coupling between the plasmon and the incident light. The characteristic propagation length of the plasmon is approximately 2 μm and 20 μm for a wavelength of 633 and 900 nm, respectively, and for a 400 μm diameter capillary tube the deviation of the plasmon at the characteristic propagation length is 0.6 and 6 degrees respectively. This means that for the longer wavelength the curvature will probably interfere with the surface plasmon coupling, but for the shorter wavelength the curvature should have little effect. For an 8 mm inner diameter vial the deviation is only 0.03 and 0.3 degrees respectively, and hence the effect from the curvature is negligible. Using other conducting materials with shorter surface plasmon propagation lengths, will lead to lower sensitivity due to broadening of the dip. A preferred inner radius is typically more than 1 mm, and is preferably 3 to 8 mm, and is typically less than 20 mm, preferably less than 10 mm.

Ellipsometric Technique

A useful measurement technique is to perform a ellipsometric readout, i.e. keep track of the changes in the polarisation state. In other words, the relative phase and amplitude between the reflection coefficients of the p-polarized and the s-polarized light is measured. The s-polarized light is the electrical field component perpendicular to the plane of incidence, also denoted transverse electrical (TE). The ellipsometric properties are often expressed as the complex (real and imaginary numbers) reflection coefficient:

$$\rho = \frac{R_p}{R_s} = \left|\frac{R_p}{R_s}\right| e^{i(\delta_p - \delta_s)} = \tan(\Psi) e^{i\Delta} \quad (9)$$

Where $$\tan(\Psi) = \left|\frac{R_p}{R_s}\right| \quad (10)$$

and $$\Delta = \delta_p - \delta_s \quad (11)$$

i.e. the polarization state can be expressed in the "ellipsometric angles" Ψ and Δ. The polarization state can be measured by both compensating (null ellipsometry) and non-compensating (photometric) ellipsometric systems. The compensating ellipsometer can use a polarizer-compensator-sample-analyzer (PCSA) setup, where the light source is placed before a rotating polarizer followed by a fixed compensator (usually a ¼ wave plate at 45°. Between the compensator and the analyzator, is the sample placed, consisting of both SPR-supporting layer and sample under test. The analyzer, is a polarizer, which is also rotating. The photo detector is placed after the analyzer. The polarizer and analyzer are independently rotated until extinction of occurs. The compensator introduces a phase shift between the p- and s-polarized light. The ellipsometric angles can be found from:

$$\Psi = A$$

and $$\Delta = 2P + 90°$$

Where A and P are the azimuths for the analyzer and polarizer, respectively. The compensating ellipsometer is not limited to this setup.

Non-compensating ellipsometer can be achieved in several ways. One is with fixed azimuths close to extinction and measurement of light intensity at the detector. Another is to use a rotating analyzer RAE, where the polarizer is fixed and the compensator is optional. By measuring both the amplitude and phase (with respect to the azimuth of the analyzer) at the detector, the ellipsometric angles Ψ and Δ can be determined.

The ellipsometric measurements can be performed with imaging optics.

The proposed configuration of the device means that it is possible to measure changes in optical parameters with an extremely high accuracy, without using any optical coupling medium, nor using complex optics, making the system very cost effective. It would also be possible to use a divergent beam as proposed by Chinowsky et al. [11], but that will require additional optics. For this case the measuring spot can be focused and it its position will be independent of the effective refractive index of the sample medium.

By using a container or a tube, an integrated flow handling system can be placed inside the container, leading to a compact, precise and cost effective solution. The macroscopic shape of the container means that it has a large sensor area, ideal for multi-spot measurements. The possibility of easy rotation of the tube/vial means that the whole sensor area can be scanned extremely fast. A rotation of the tube/vial gives also the opportunity to use the centrifugal force to move samples. A typical flow cell height is preferably between 10 and 100 µm and more preferably between 20 and 50 µm.

The shape of the insert makes it suitable for temperature control of the sample. There are at least three reasons for temperature control: 1) Reaction kinetics is temperature dependent, 2) Resemble In Vivo conditions, e.g. 37 degrees C., 3) Baseline of SPR-signal is temperature dependent. If a reaction is following the Arrhenius Rule every 7 (or 10) degrees C. increase in temperature will double reaction rate. In case of water based buffer, SPR base line will change approximately −100 micro refraction units for every degree C. An increase in temperature will decrease the refraction unit due to thermal expansion. The configuration of the invention makes it possible to place thermal control close to the sensor surface and hence a good thermal conductivity can be obtained leading to precise thermal control. One embodiment uses a liquid, e.g. water, water/glycol, etc, to transfer heat/cold to the sample area. The sample heat unit in the insert is placed very close (typical within 1 mm) to the roof of the flow cell, making temperature control very fast and precise. Temperature controlling liquid is flowing at the outer part of the sample temperature unit leading to very low thermal resistance to the sample. The temperature controlling liquid is preferably heated or chilled by a thermoelectric element. But, other temperature regulating devices such as compressor-condenser, or just tap water, are alternatives. If only heating is required a resistive element (Joule heating) is preferred. Another embodiment with only heating is using resistive heating close to the sample area, without using circulating liquids, and only use thermal conduction to temperate the sample.

Another embodiment uses two or more temperature controlling liquids, when switched into the sample temperature unit, making fast temperature steps or precise temperature ramps with respect to time.

Yet another embodiment uses different temperatures at different places on the sample temperature unit, which will create a well defined temperature gradient due to the thermal conductivity of the sample temperature unit.

Because of the rotational symmetry and macroscopic radius and a relatively short height, the tube is very easy to manufacture with high optical standards and high mechanical precision. The dimensions of the tube/vial make it easy to deposit the essential surface plasmon carrying metal film with a high precision at a low cost.

The present invention provides a device and apparatus for measurement of refractive indices close to the inner surface of a tube, cup or vial or a part thereof, based on surface plasmon resonance. The sensing surface may consist of one or a plurality of sensing areas, in axial or radial or diagonal direction or a combination of these directions. The specimen under investigation may be studied in a gaseous, liquid or solid environment. The device can be used for concentration measurement of gases or analytes in a liquid. The device can also be used for analyses of interaction between molecules, e.g. biomolecules. The device can be used for measurement of changes in conformation of a specimen, e.g. coagulation of blood. The device can be used for monitoring of adlayer formations.

DEFINITIONS

For the purpose of this invention a "flow structure" is taken to mean any structure that cooperates with the inner surface of the sensor unit in such a way as to provide a reduced sample volume in the cavity of the unit.

Non-limiting examples of a such a flow structure are an insert forming an annular space in a cylindrical sensor unit, or an insert provided with grooves or recesses forming flow channels when the insert rests against the inner surface of the sensor unit.

The function of such inserts is to direct the sample, to limit the extension of the sample within the unit, or to adjust the height from sensor surface of e.g. a flow cell, provided by the insert, in order to control the diffusion of sample analyte to the sensor surface, or for controlling the flow rate across the sensor surface.

A "cavity" shall be taken to mean a space that is surrounded by something, although it need not, but can be completely surrounded.

A "compartment" shall be taken to mean the space wherein a sample is located, i.e. the space formed in cooperation between an insert and the inner surface of the sensor unit.

The invention will now be described, but not limited, with reference to the drawings.

FIG. 1a illustrates one embodiment of the apparatus of the invention wherein a collimated input beam 300 emanates from an illumination system 400 onto a sensor unit 100, containing a specimen under test 200, such as a liquid sample or a gas, directed by a structure 610, and the reflected light 330 is measured by a detection system 500. The sensor unit 100 has a transparent substrate 103, typically a plastic material or glass, which is rotationally symmetric or partly rotationally symmetric. The inner surface of the substrate 103 is covered with a thin, typically 50 nm, conducting layer 110 of a free electron like material, typically gold or silver, which can conduct a surface plasmon. The incident light 300 is refracted 310 at the outer surface of the substrate 103, onto the inner surface and the conducting layer 110, where the light is either reflected 320 or absorbed in the conducting layer 110 by a surface plasmon, or a combination of both. The reflected light 320 is then refracted at the outer surface of the substrate 103, forming a light-beam 330 which impinges on a detector system 500. The optical detection system 500 incorporates a photon sensitive device 510, that may be a photographic film, but is preferably a photo-detector, e.g. a charge coupled device (CCD), charge injection device (CID), CMOS-device, photo diode etc. For the case of using the photo detector 510, the optical signal is evaluated by an electronic device 800, preferably a computer system incorporating an analog to digital converter. The illumination system 400 incorporates at least one light source 410, but also a plurality is possible, that may be a laser, light emitting diode (LED), gas discharge lamp (e.g. Xenon), tungsten halogen lamp etc., or an array or matrix of the elements. The light source 410 may create a polarized light, e.g. some lasers, or a polarizing element 420 may be inserted anywhere within the light path. The polarization is preferably p-polarised (transverse magnetic mode) with regard to the inner surface of the sensor unit 100 for reflectance measurements. The polarizing element 420 can be a dichroic sheet, Glan-Taylor prism, Glan-Thompson prism, or an equivalent device. However, the light beam does not necessarily have to be polarized, but that will enhance signal to noise ratio. The light beam 300 is in this configuration expanded by an optical element 430, e.g. lenses or diffractive optical elements (DOE's), or a combination of both, creating a line pattern, making it possible to simultaneously monitor a line (axial) at the sensor surface 110.

Figure 1B:
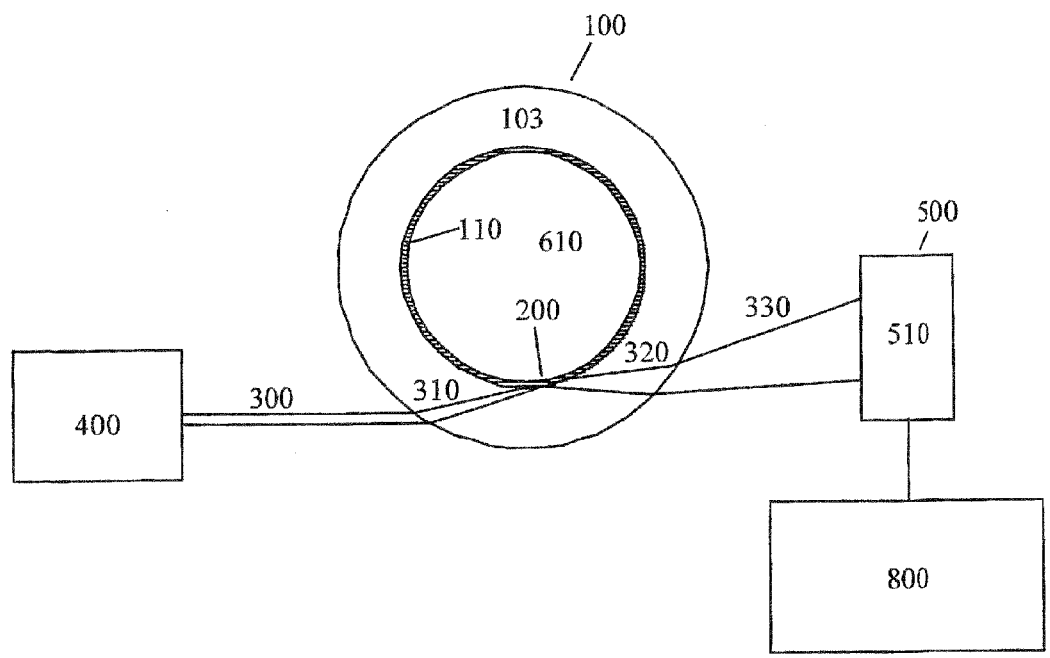
FIG. 1b shows an apparatus for surface plasmon resonance measurements with a line shaped beam (top view) without an imaging lens.

FIG. 1b illustrates the same configuration as FIG. 1a, but with a view from above.

Figure 1C:
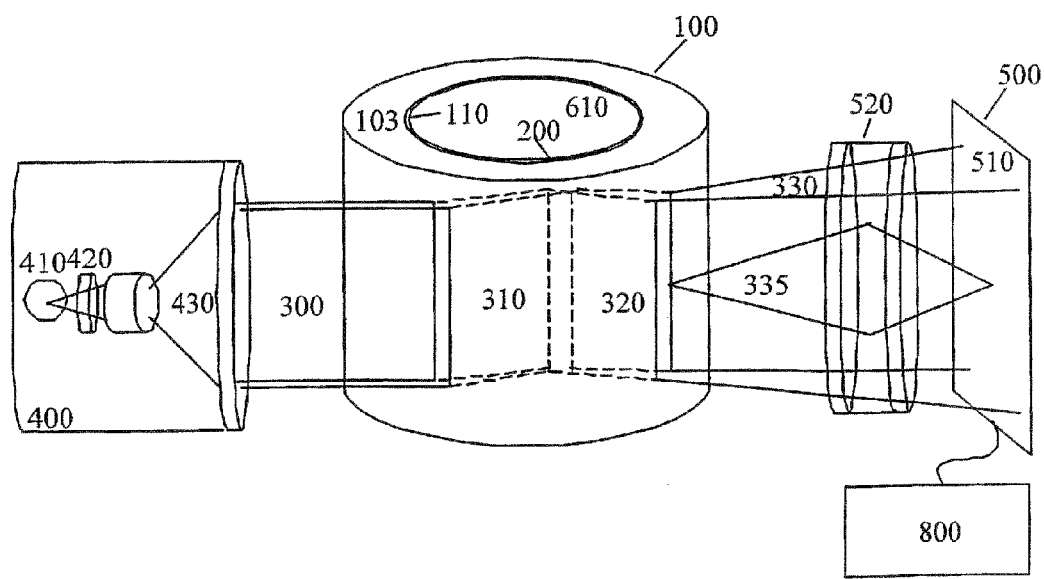
FIG. 1c shows an apparatus for surface plasmon resonance measurements with a line shaped beam (tilted view) and an imaging lens.

FIG. 1c illustrates an apparatus with imaging optics 520. The imaging optics 520 will image the sensor surface 110 axially. The imaging optics will collect the angular spectrum 335 from each point on the sensor surface and focus the rays onto the detector 510. The imaging optics 520 will minimize the effect from diffraction effects due to uneven reflectance distribution along the sensor surface 110, or by obstruction of the optical wave propagation. The imaging optics 520 preferably contains at least one cylindrical lens or on equivalent DOE.

Figure 1D:
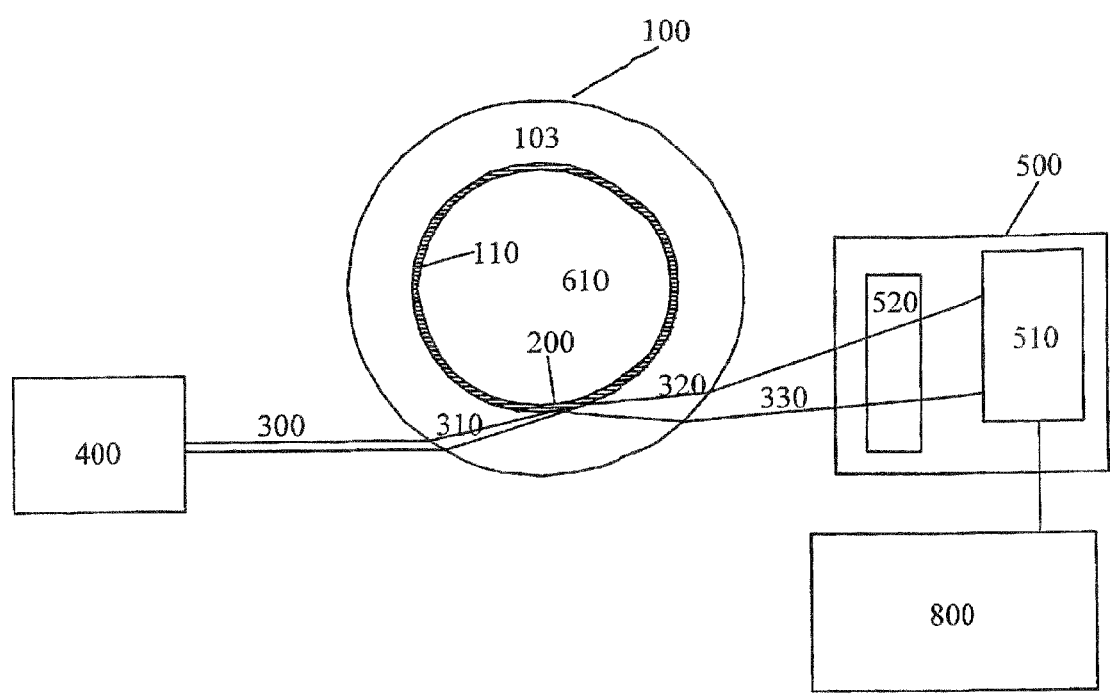
FIG. 1d shows an apparatus for surface plasmon resonance measurements with a line shaped beam (top view) and an imaging lens.

FIG. 1d, illustrates the same configuration as FIG. 1c, but with a view from above.

Figure 1E:
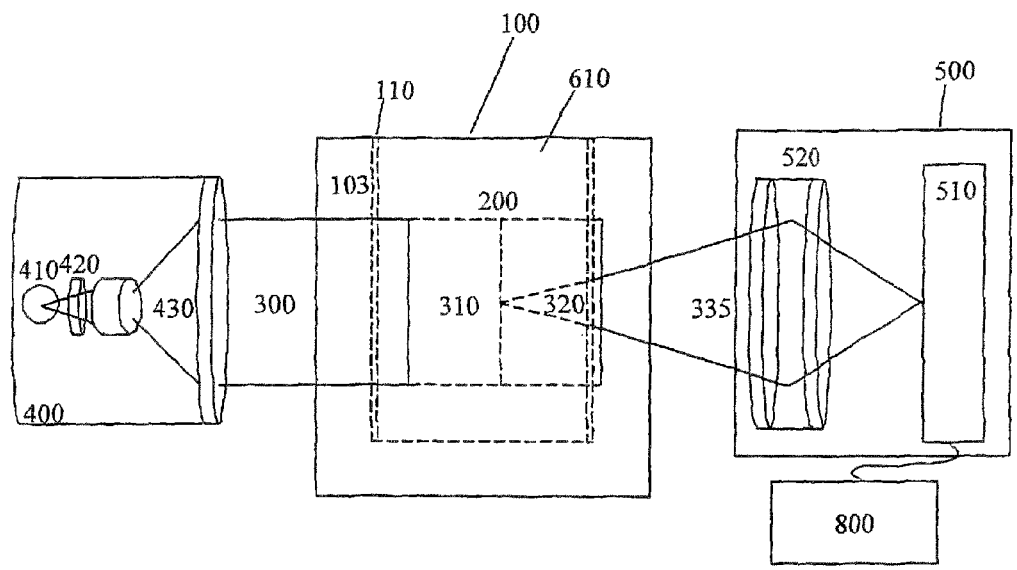
FIG. 1e shows an apparatus for surface plasmon resonance measurements with a line shaped beam (side view) and an imaging lens.

FIG. 1e, illustrates the same configuration as FIG. 1c, but with a cross section of the sensor unit.

Figure 2:
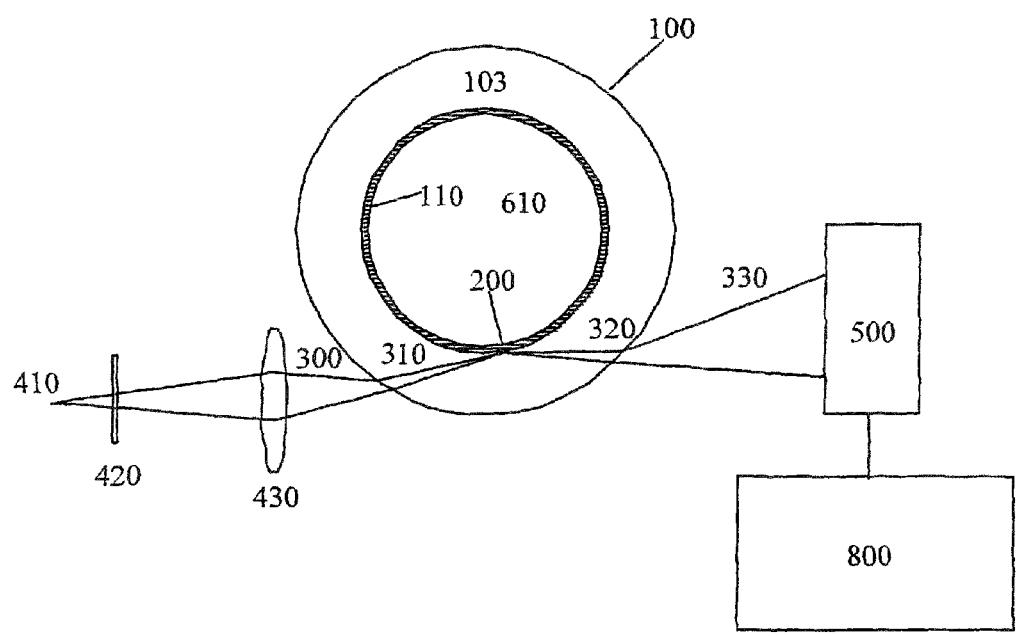
FIG. 2 shows an apparatus for surface plasmon resonance measurements with a focused fan-shaped beam.

FIG. 2, illustrates an apparatus utilizing a convergent beam (fan shaped beam), 300 and 310, to focus on a specific spot at the sensor surface 110. By using a convergent beam the position of the sensor spot can be small and independent of the resonance condition, i.e. all incident angles impinge on the same spot on the sensor surface 110.

Figure 3A:
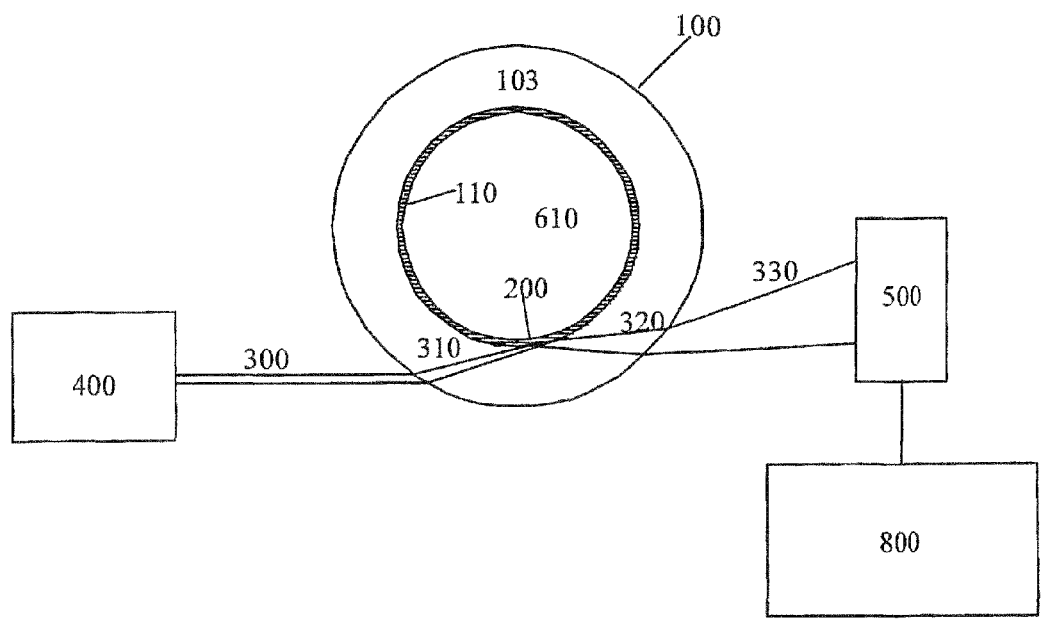
FIG. 3a shows an apparatus for surface plasmon resonance measurements with a gaussian, circular shaped beam, side view.

FIG. 3a, illustrates an apparatus with a collimated or nearly collimated beam 300 from a light source 400. The light source is preferably a laser or LED. The curvature of the substrate 103 will convert the collimated beam 300 to a convergent beam 310, with respect to the surface normal of the sensor surface 110. The collimated beam will, due to general physics laws, have a gaussian intensity profile, which is not a disadvantage, but rather an advantage making it possible to just illuminate the angles where the surface plasmon can be excited. The specimen under test 200 is directed by a structure 610.

Figure 3B:
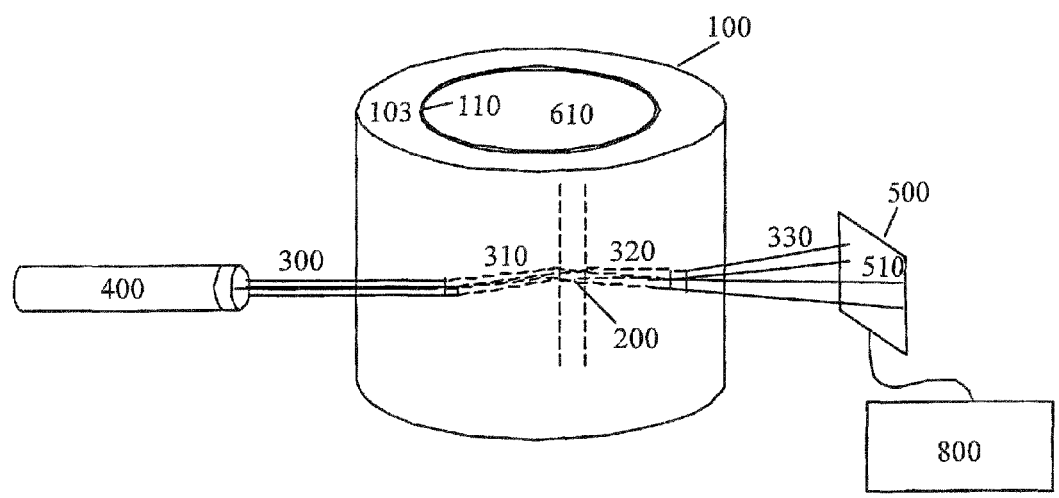
FIG. 3b shows an apparatus for surface plasmon resonance measurements with a gaussian, circular shaped beam, perspective view.

FIG. 3b, illustrates the configuration of FIG. 3a, but seen from a perspective view.

Figure 4:
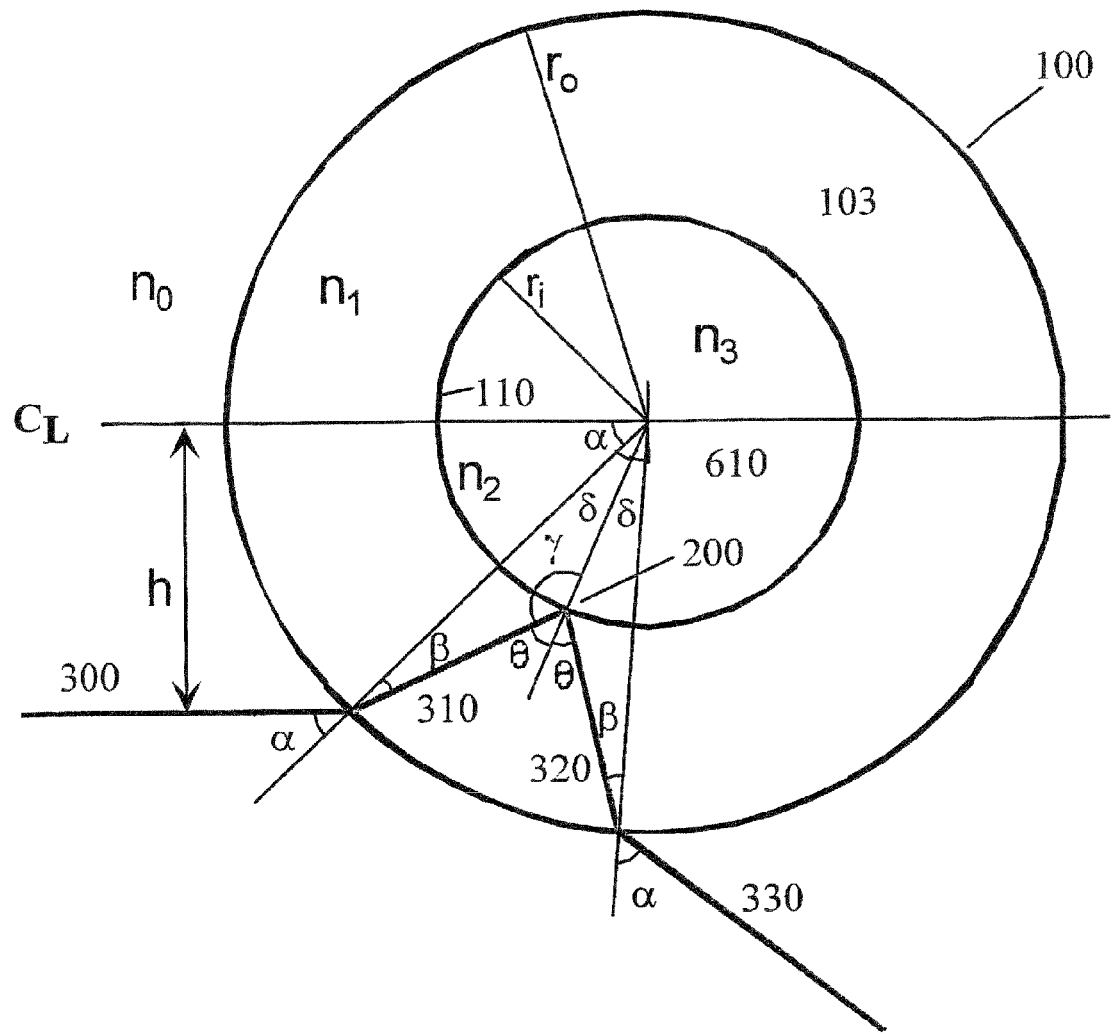
FIG. 4 shows the angles of the incident and the reflected beams.

FIG. 4, illustrates the optical path in the sensor unit 100. The substrate 103 has a refractive index of $n_1$ and an outer and inner diameter of $r_o$ and $r_1$ respectively. The ambient medium, typically air, has a refractive index of $n_0$. An incident beam 300 impinges on the substrate 103 at an incident angle, $\alpha$, relative the surface normal. The incident angle, $\alpha$, is controlled be the height, h, from a centerline, $C_L$, parallel to the beam 300, by the formula:

$$\alpha = \arcsin\left(\frac{h}{r_o}\right) \quad (9)$$

The beam 300 is refracted into a refracted beam 310 with an angle of $\beta$ relative the surface normal according to Snells Law:

$$n_0 \sin \alpha = n_1 \sin \beta \quad (10)$$

The refracted beam 310 will impinge on the inner surface of the substrate at an incident angle $\theta$. The angle $\theta$ is denoted the resonance angle $\theta_{SP}$ at a match of the momenta of the incident light 310 and the surface plasmon. According to optical laws the exit angle $\theta$ of the reflected beam 320 is equal to the incident angle $\theta$ of the incident beam 310. Due to symmetry, the incident and refracted angles, $\beta$ and $\alpha$ respectively, at the substrate-ambient interface for the outgoing beam 320 and 330 will be the same as the refracted and incident angle, $\beta$ and $\alpha$ respectively for the incident beam 300.

The substrate 103 is coated with a conducting layer 110 with refractive index $n_2$. The specimen under test 200 is usually a gas or liquid with an effective refractive index of $n_3$, which is directed towards the conducting layer 110 by a flow controlling structure 610.

Figure 5:
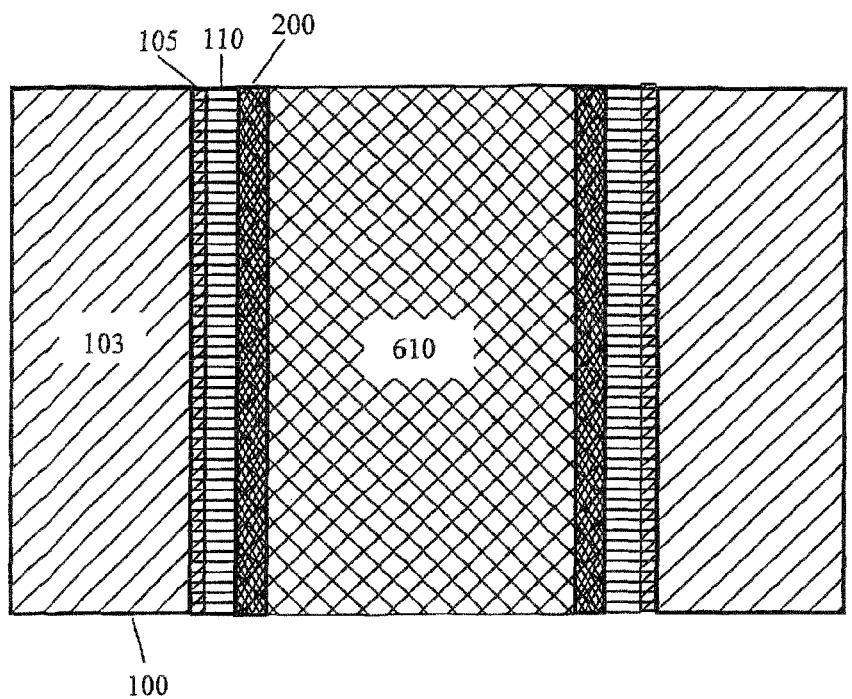
FIG. 5 shows a sensor unit with adhesion layer and metal coating.

FIG. 5 illustrates the sensor unit 100 with an adhesion layer 105 between the substrate 103 and the conducting layer 110. The adhesion layer is thin, typically less than 2 nm and preferably 0.5 nm, which means that it is thick enough to assure good adhesion and thin enough, not disturbing the surface plasmon. The adhesion layer 105 is typically titanium or chromium.

Molecular Recognition Layer

Figure 6:
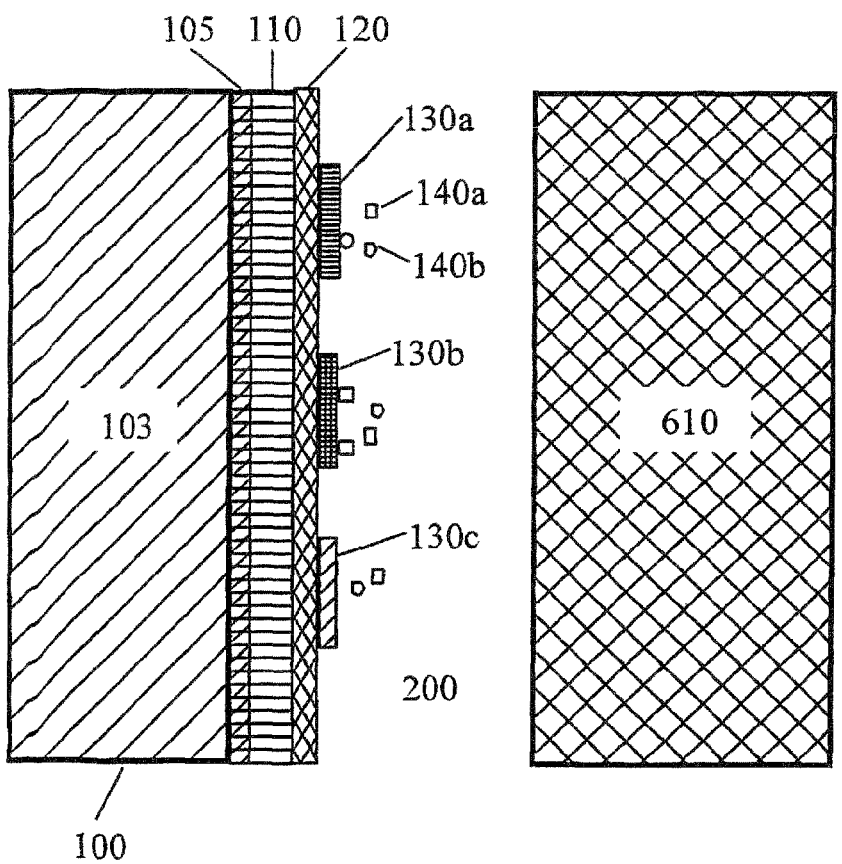
FIG. 6 shows a sensor unit with different molecular recognition layers.
Figure 7:
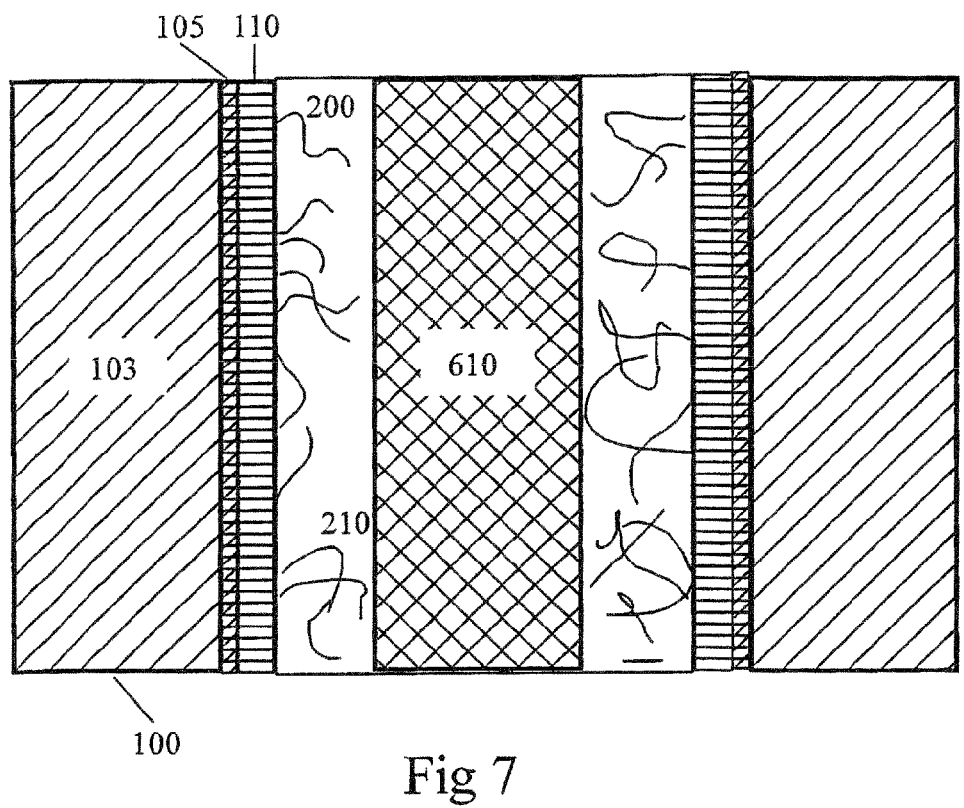
FIG. 7 shows a sensor unit measuring a polymerization/depolymerization, with or without oscillation of the cup/vial.

FIG. 6 illustrates the sensor unit 100 with one or a plurality of molecular recognition area/areas 130a-c. The molecular recognition areas 130a-c are typically specific to analytes 140a-c respectively. The molecular recognition layer 130 is typically attached to the conductive layer 110 by the means of a linker layer 120. The linker layer 120 is typically an alkanethiol with a carbon chain length greater than three and preferably 16, using the thiol groups to bond to the gold surface. The linker layer 120 may incorporate a hydrogel 210, as shown in FIG. 7. The linker layer 120 may incorporate avidin/streptavidin biotin molecules. When the analyte molecules 140 binds to the recognition layer 130, the dipoles at the analyzing frequency within the probe depth of the surface will normally increase and hence increase the effective refractive index $n_3$ of the specimen under test 200. The increase of $n_3$ will increase the propagation constant of the surface plasmon, i.e. the resonance condition will change. The specimen under test 200 is held between the substrate and the structure 610.

FIG. 7. illustrates a polymer layer 210, fibrin etc. The polymer formation can be supervised in conjunction with a rheometer, i.e. the cup or vial is rotating or oscillating, e.g. free oscillating rheometer (FOR).

Figure 8:
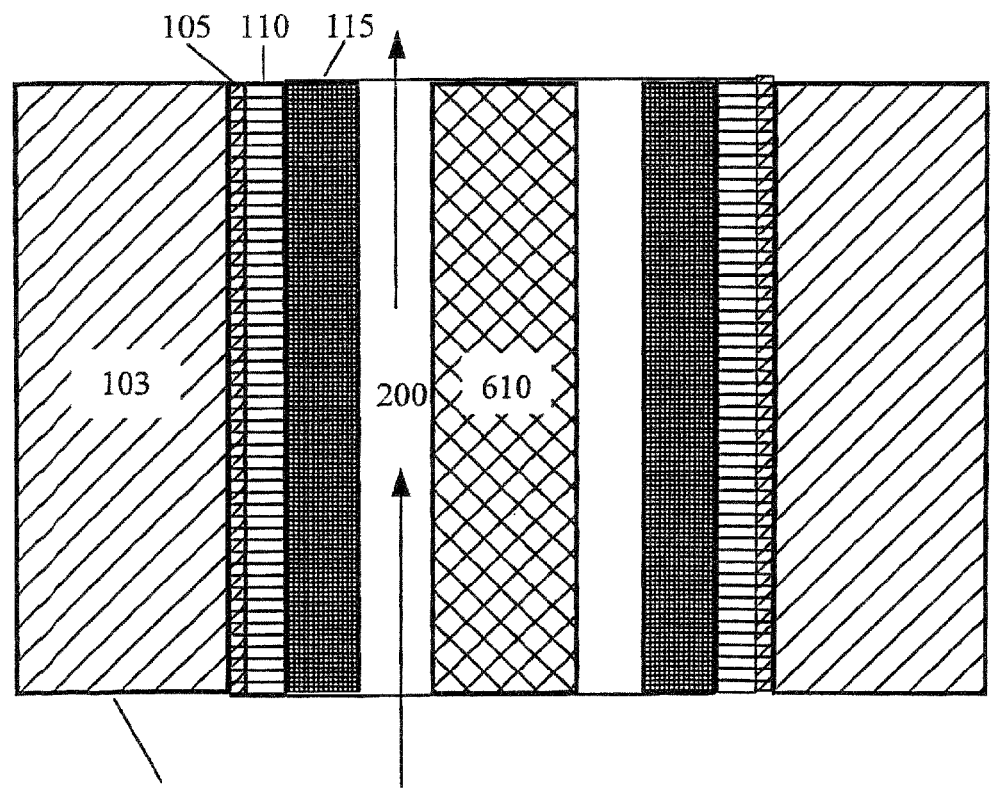
FIG. 8 shows a sensor unit with a polymer sensing film for gas or liquid recognition.

FIG. 8 illustrates a sensor unit 100 with a polymer layer 115 as the recognition layer. The polymer layer 115 is sensitive to the specimen under test 200, which is either a gas or liquid. The polymer 115 will either be denser or less dense upon contact with the specimen 200. A denser polymer will increase the effective refractive index $n_3$. The polymer film can be made of polyflouroalkylsiloxane, and the gases can be halogenated hydrocarbons such as trichloroethylene, carbon tetrachloride, chloroform, methylene chloride, etc.

Figure 9A:
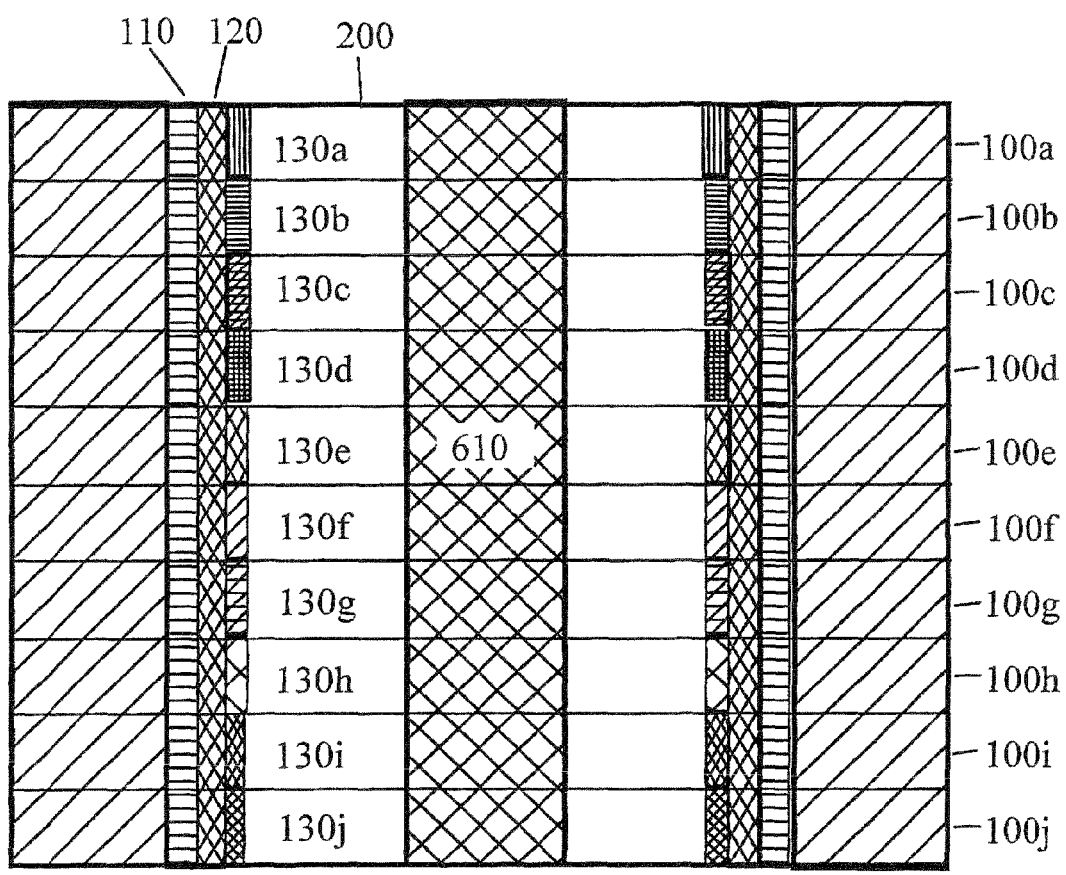
FIG. 9a shows a sensor unit consisting of slices with different molecular recognition layers.

FIG. 9a illustrates the sensor unit 100 incorporating slices 100a-j containing different sensing layers 130a-j attached preferably to a linker layer 120, however the linkerlayer can be omitted.

Figure 9B:
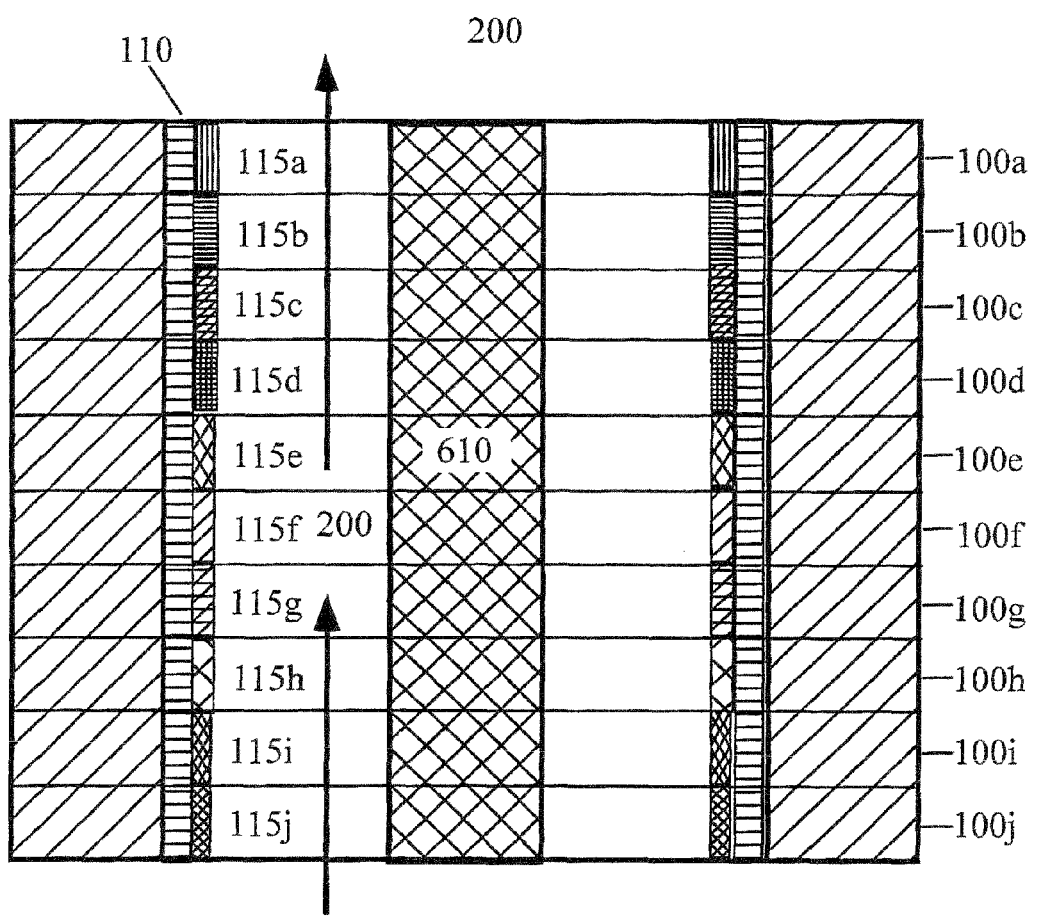
FIG. 9b shows a sensor unit consisting of slices with different molecular recognition layers where the analyzing medium is flowing through the device.

FIG. 9b illustrates the sensor unit 100 incorporating slices 100a-j incorporating different polymer sensing layers 115a-j.

Figure 9C:
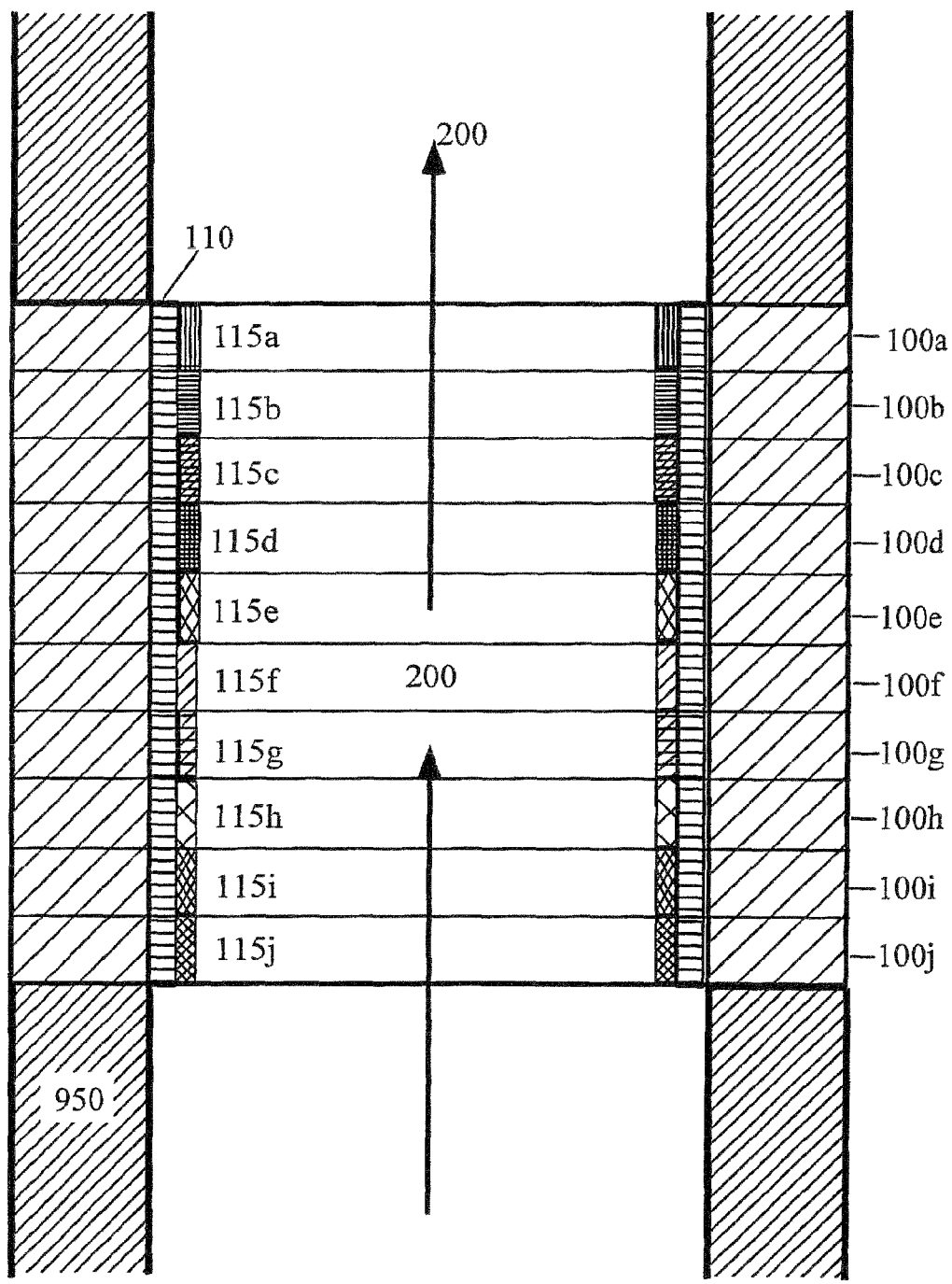
FIG. 9c shows a sensor unit consisting of slices with different molecular recognition layers fitted into a tube.

FIG. 9c illustrates the sensor unit 100 incorporating slices 100a-j incorporating different polymer sensing layers 115a-j, inserted into a tube.

Rotable Sensor Unit

Figure 10A:
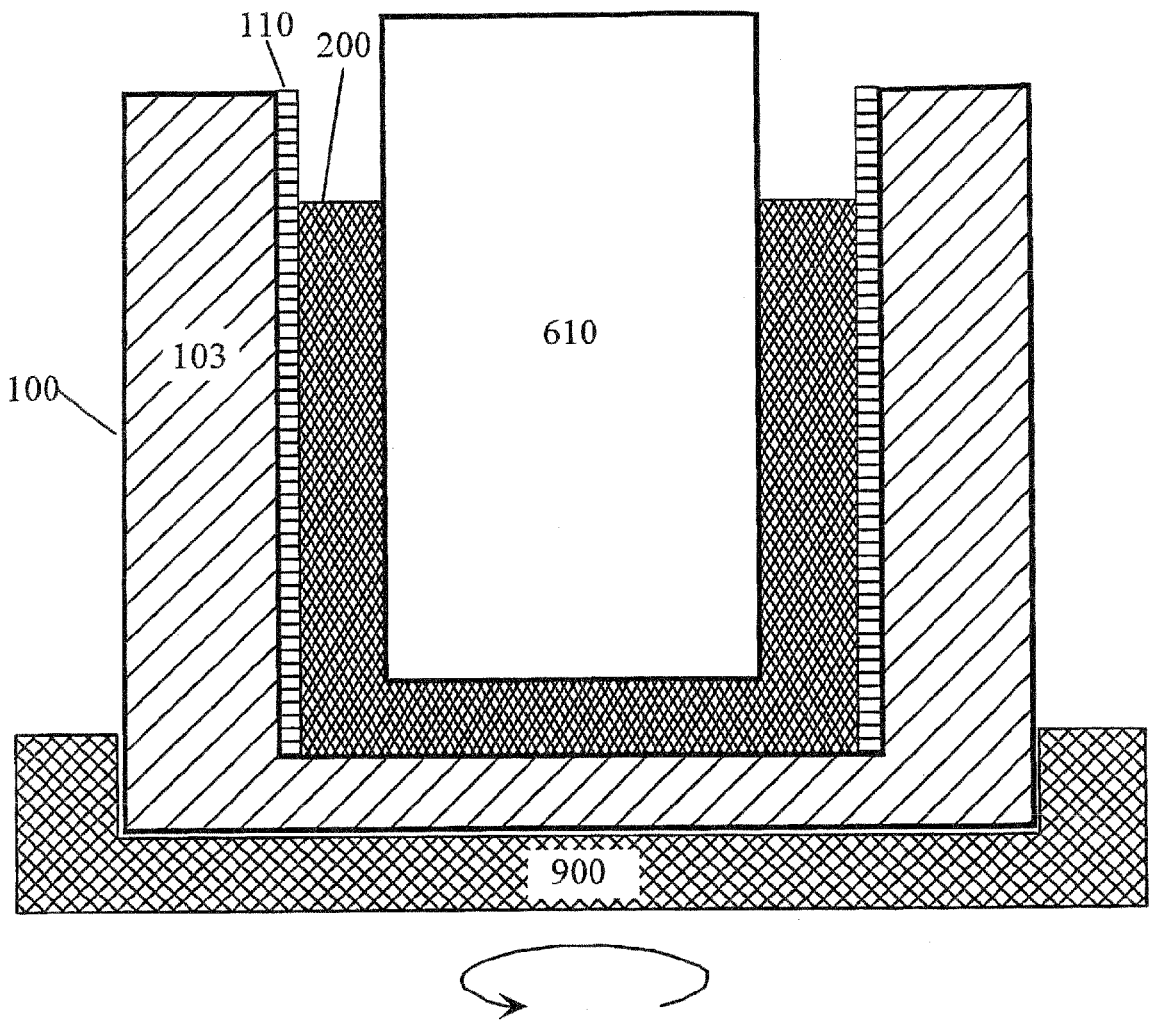
FIG. 10a shows an apparatus where sensor unit is rotating.

FIG. 10a illustrates a sensor unit 100, which rotates. The rotation of the sensor unit 100 means that the whole sensing surface 110 can be scanned. A rotating sensor unit 100 means that the surface concentration at the inside of the device is monitored fast for many sensing spots or e.g. gradients.

Figure 10B:
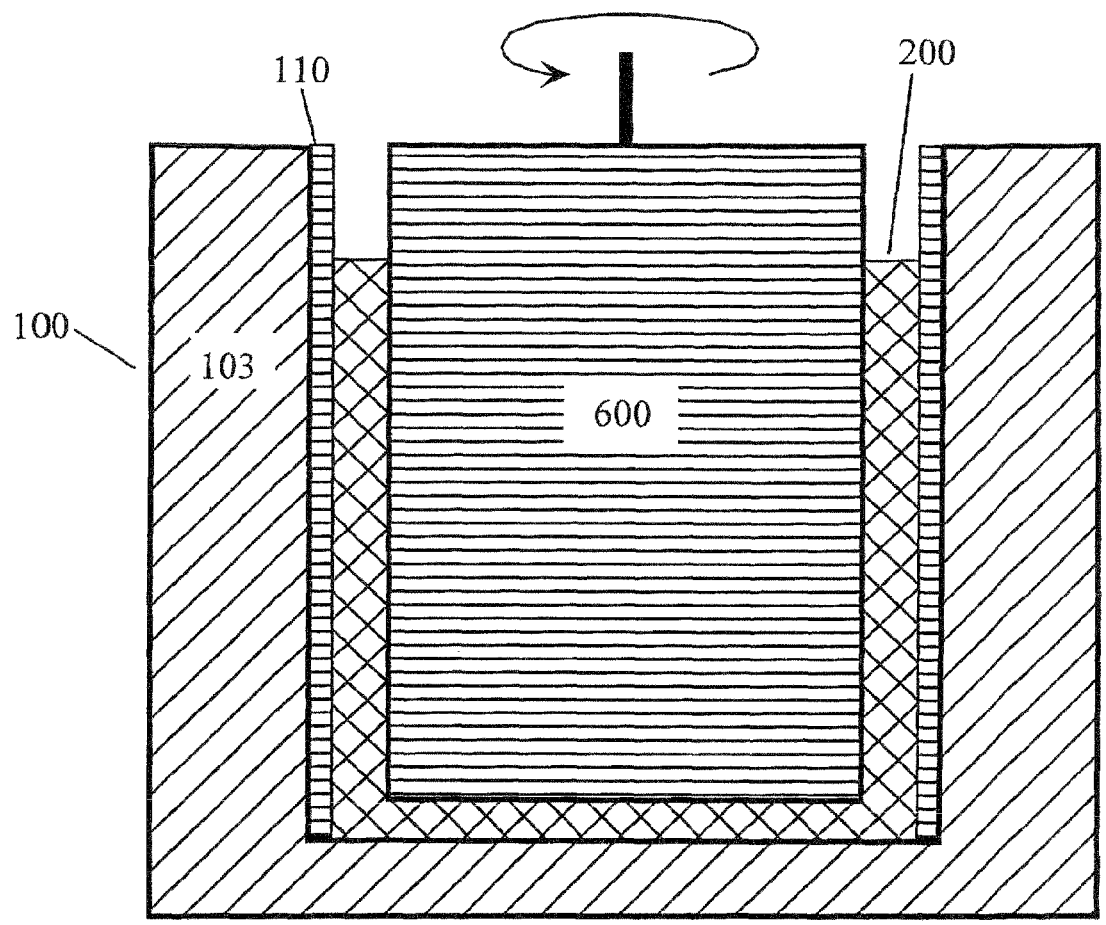
FIG. 10b shows an apparatus where a rotating bob is inserted inside the sensor unit.

FIG. 10b illustrates the same set up shown in FIG. 10a, but with a rotable bob 600 inserted into the cavity of the sensor unit. The rotating bob introduces shear rates in the specimen under test 200. The bob will also reduce the sample volume of the specimen under test 200. The bob 600 can also be fixed to reduce the sample volume 200.

Figure 10C:
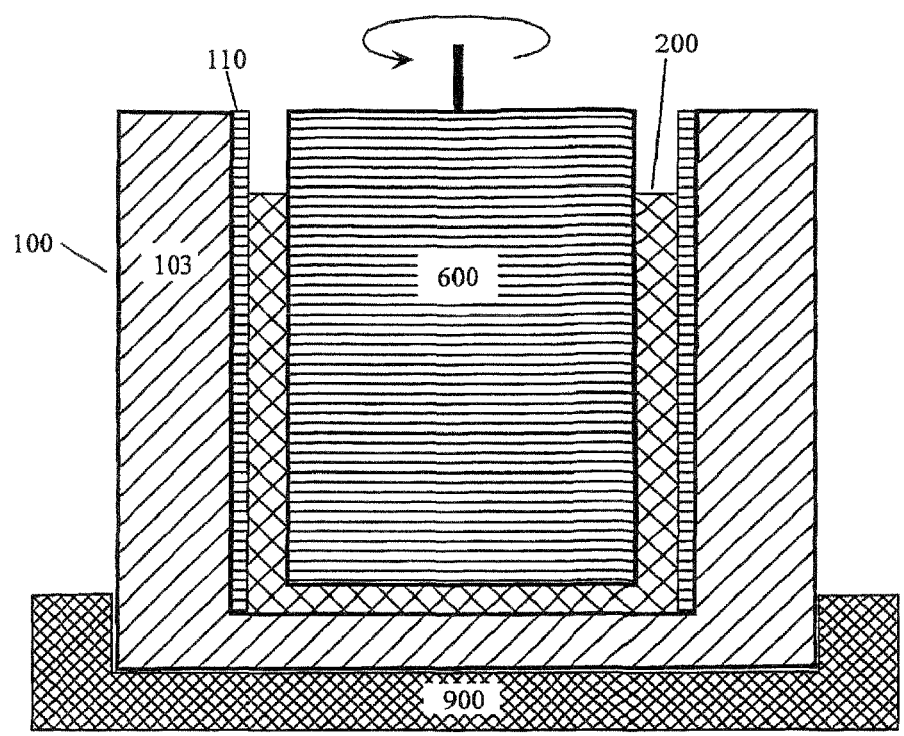
FIG. 10c shows an apparatus where a rotating bob is inserted inside a rotating sensor unit.

FIG. 10c illustrates the same set up shown in FIG. 10b, but with a rotating or fixed bob 600 and a rotating or fixed sensor unit 100.

Figure 11:
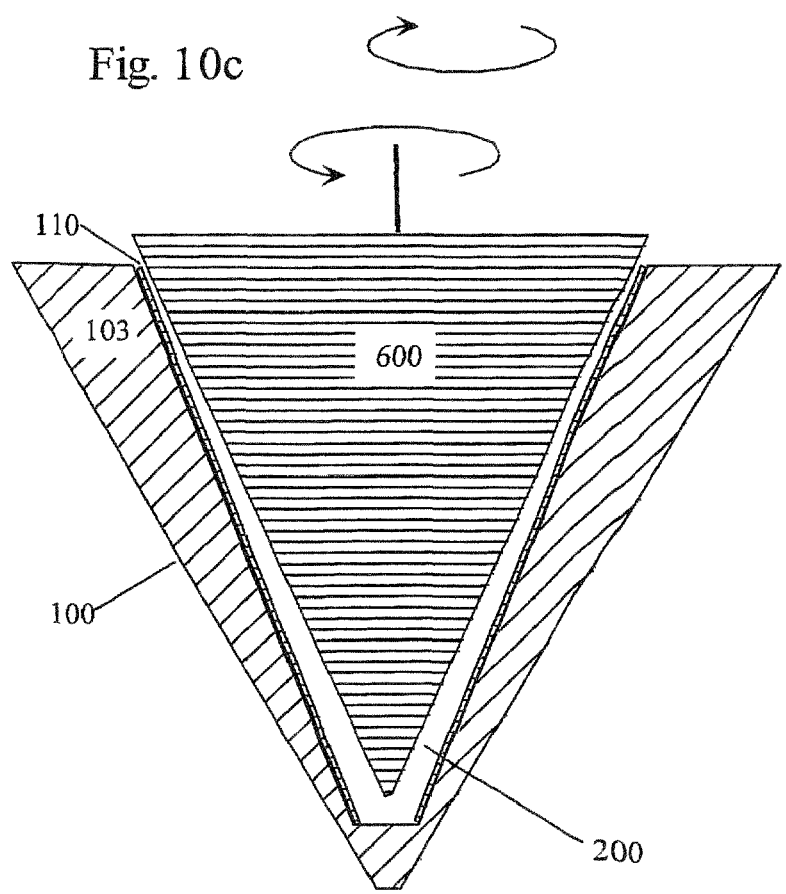
FIG. 11 shows a sensor unit with a conical shape.

FIG. 11 illustrates a similar setup to FIG. 10b, but with a conical sensor unit 100 and a conical bob 600. The conical set up will introduce different shear rates along the axis, which will e.g. affect a polymerization process monitored by surface plasmon resonance. This is particularly interesting for studies of the hemostasis system. The conical sensor unit 100 will obtain a larger dynamic range of share rates if conical shape of the substrate 103 and the bob are different, as illustrated in FIG. 11.

Micro Fluidic Insert

Figure 12A:
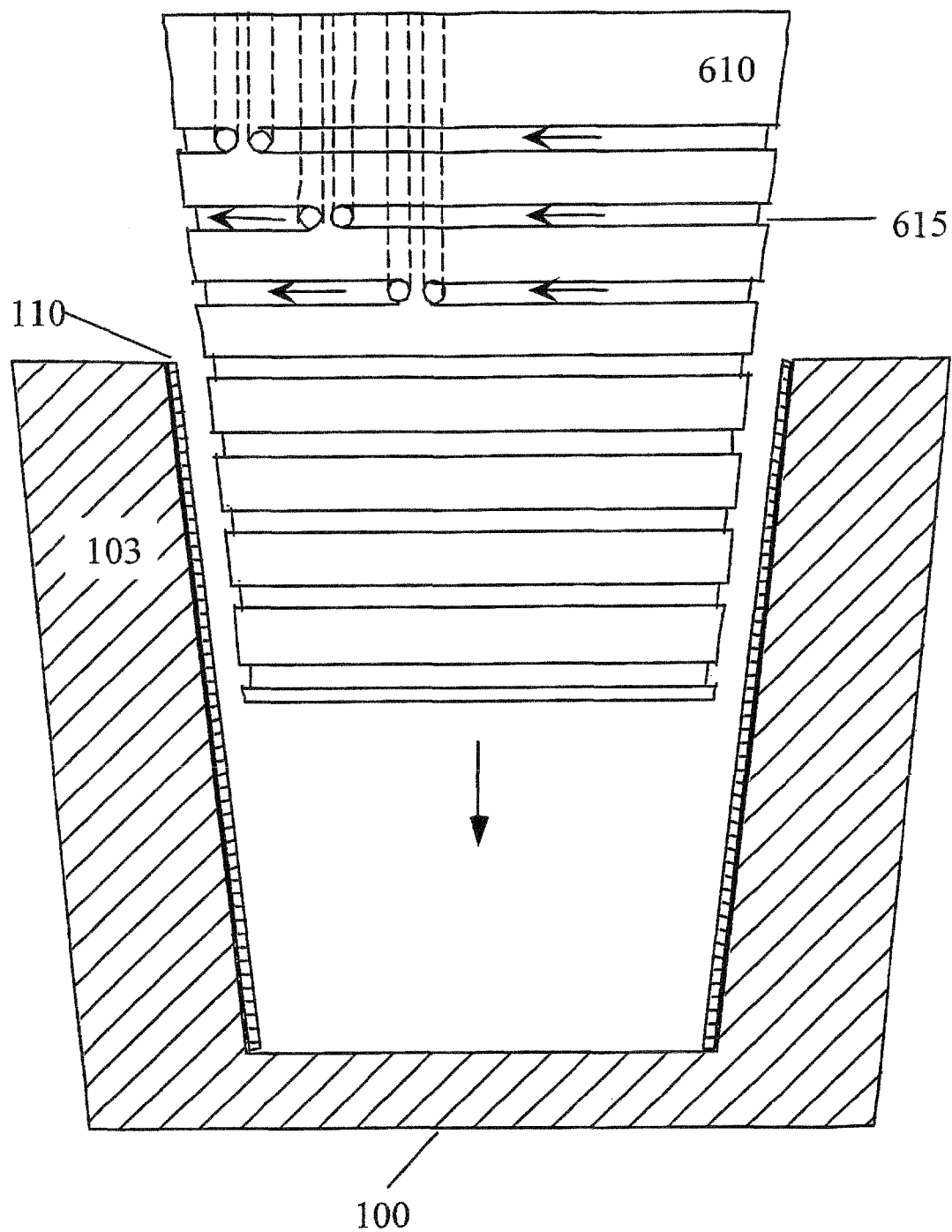
FIG. 12a shows a device with an interchangeable radial fluidic insert.

FIG. 12a illustrates a sensor unit 100 with a fluidic insert 610 to be inserted into the substrate 103.

Figure 12B:
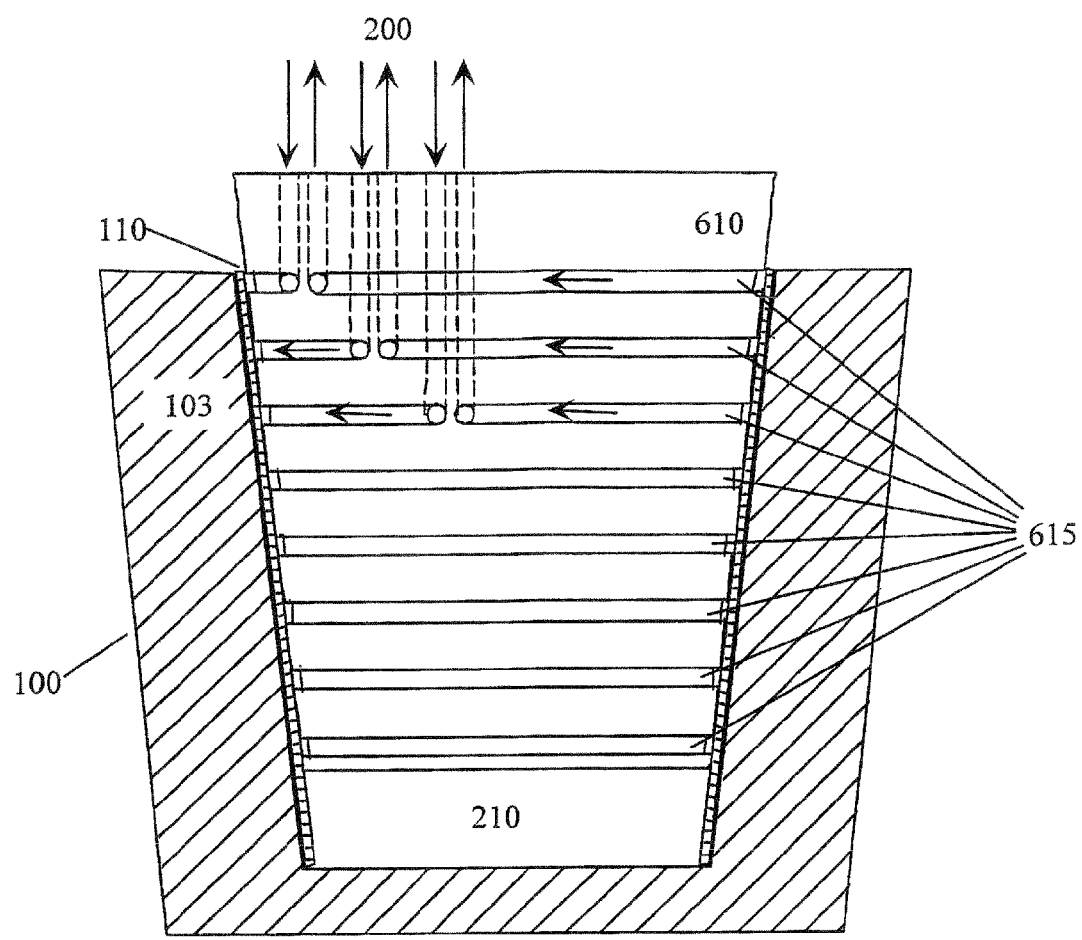
FIG. 12b shows a device with a radial fluidic insert.

FIG. 12b illustrates the sensor unit 100 with the fluidic insert 610. The fluidic insert 610 has radial channels 615, which can be used for both immobilized molecules for the recognition layer, or for analyte molecules. The substrate 103 may be conical to assure good sealing to a conical insert 610, but the substrate 103 can also be cylindrical, utilizing a cylindrical insert 610. The substrate could be made of an elastic material e.g. silicon rubber, or made of a rigid material with elastic sealings 118, as illustrated in FIG. 12c.

Figure 12C:
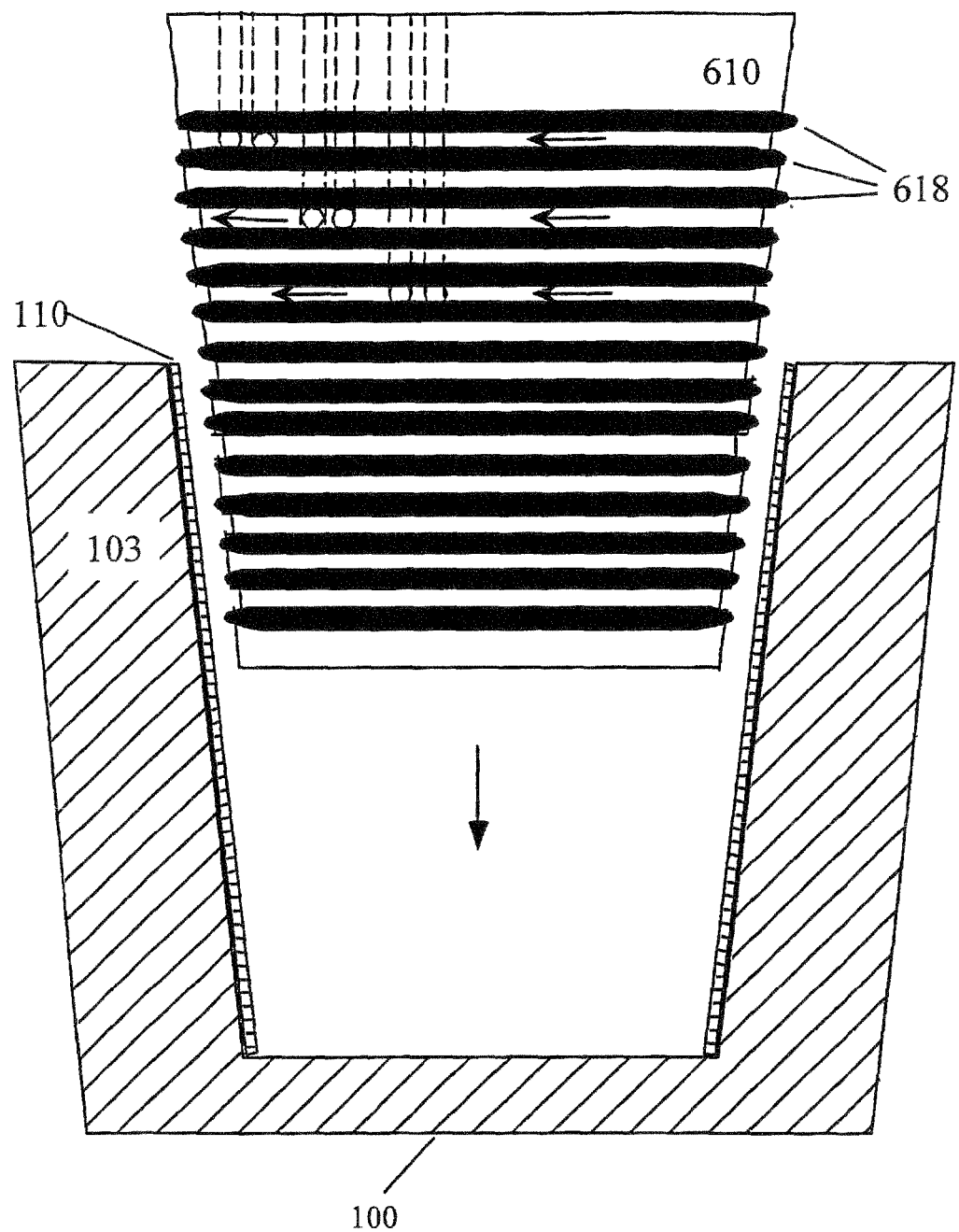
FIG. 12c shows a device with a fluidic insert utilizing seals.

FIG. 12c illustrates the fluidic insert 610 with elastic seals 618, e.g. o-rings. The substrate 103 and the insert 610 can either have a conical or cylindrical shape.

Figure 13A:
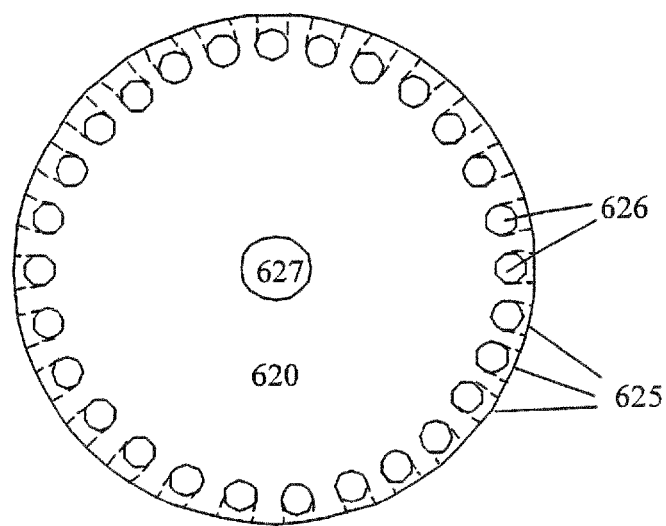
FIG. 13a shows an axial fluidic insert.
Figure 13B:
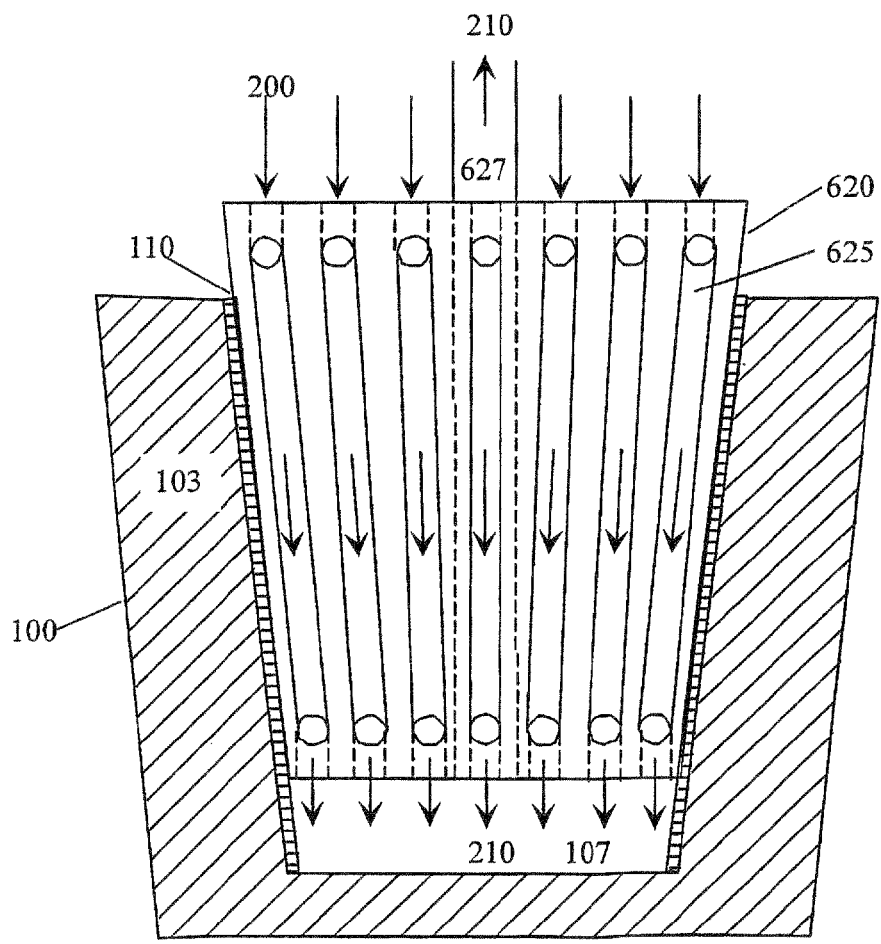
FIG. 13b shows a device with an axial fluidic insert.

FIG. 13a-b illustrates the sensor unit 100 with a fluidic insert 620 incorporating axial flow channels 625. The insert 620 may create a cavity 107 which can contain the waste 210 after performed analysis. The waste may be drained by a channel 627. The flow channels 625 may be fed by individual tubes 626, that may be filled, e.g. by an external tube, needle or syringe tip. The tube 626 may be sealed by a membrane or an ordinary elastic seal. Rotation of either the units 103 and 610 or external tubes may act as valves, changing flow cells.

SPR Curves

Figure 14:
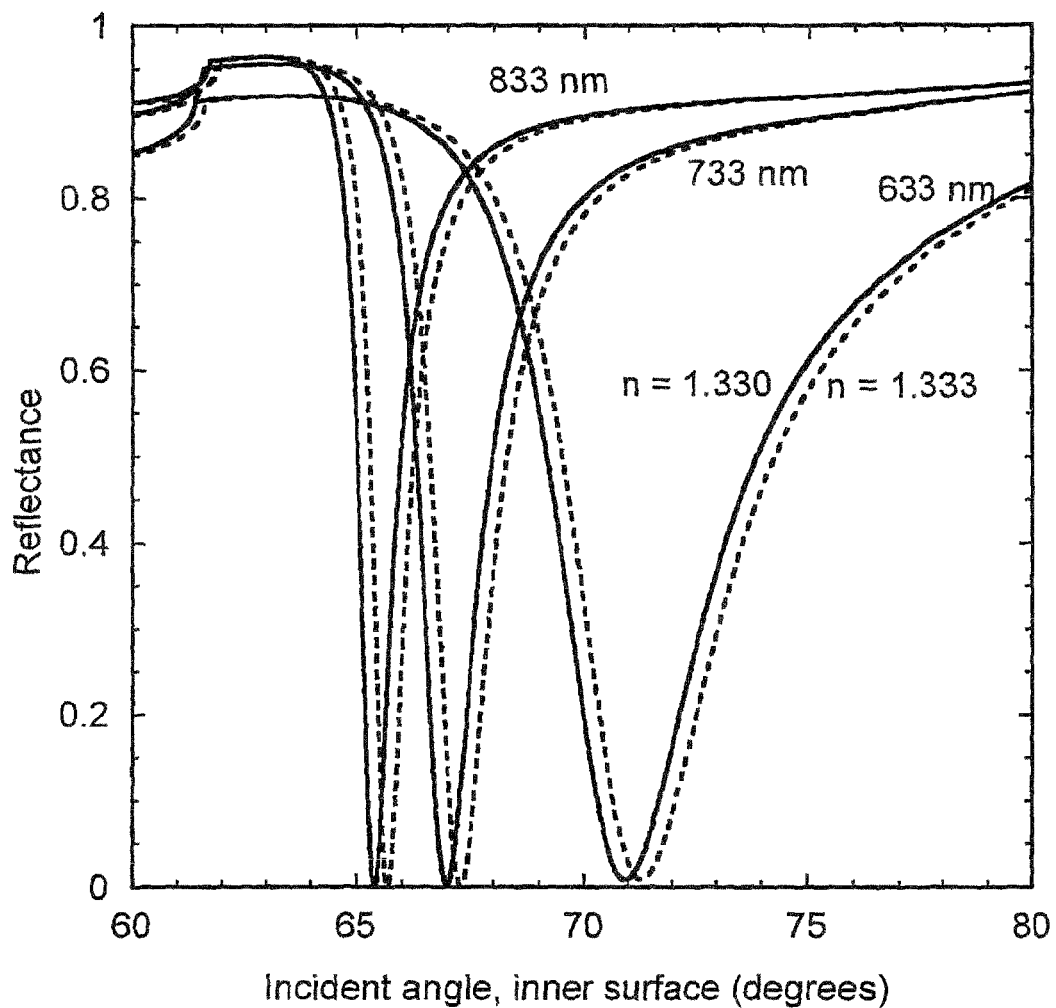
FIG. 14 shows the relation between reflectance and the inner incident angle for three different wavelengths (633, 733 and 833 nm) for two different effective refractive indices (1.330 and 1.333).

FIG. 14 illustrates calculation of the reflectance, i.e. the ratio between the incident light 310 at the sensing surface 110 and the reflected light 320 from the sensing surface 110 versus the incident angle at the inner surface of the substrate 103, for three different wavelengths, 633 nm, 733 nm, and 833 nm respectively, and two different effective refractive index, $n_3$, ($n_3$ is equal to 1.330 and 1.333 respectively) of the specimen under test 200. The conducting layer 110 is in this case gold with a thickness of 50 nm. The substrate 103 is in this case BK7 glass, with a refractive index $n_1$ of approximately 1.5. The position of the SPR-curves is a function of the effective refractive index $n_3$ seen by the surface plasmon.

Figure 15:
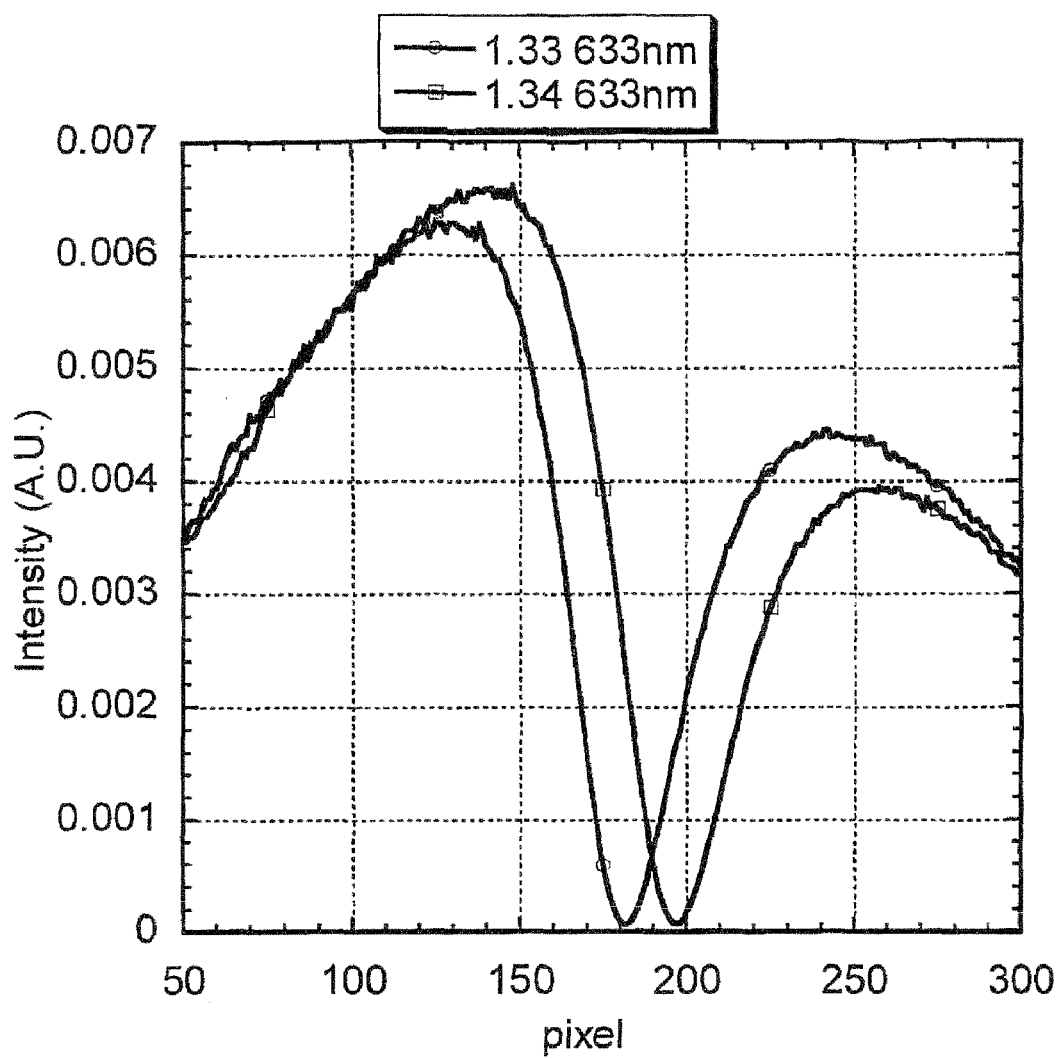
FIG. 15 shows the reflected intensity at the detector for two different refractive indices of the sample (n=1.33 and n=1.34), due to the surface plasmon at the inside of the wall of a cylindrical device, when a monochromatic light source at 633 nm is used.

FIG. 15 illustrates simulations of the reflected intensity at a detector 510 shown in FIG. 3, at a wavelength of 633 nm, where the substrate 103 is made of BK7 glass, and a 50 nm thick conduction layer 110 made of gold is applied onto the inside of the substrate 103. The refractive indices $n_3$ of the specimen under test 200 are 1.33 and 1.34 respectively. The fall off of the intensity at the border of the detector 510 is an effect of the gaussian shape of the input beam 300. The irregular shape of the curves emanates from photon shot noise.

Incident Angles at the Outer and Inner Surfaces

The incident angle, $\theta$, at the inner surface of the substrate 103 depends on the incident angle, $\alpha$, at the outer surface, the refractive indices of the ambient environment and the substrate, $n_0$ and $n_1$ respectively, and the ratio between the radii of the inner and outer surfaces, $r_i$ and $r_o$ respectively, according to equation 8.

Figure 16:
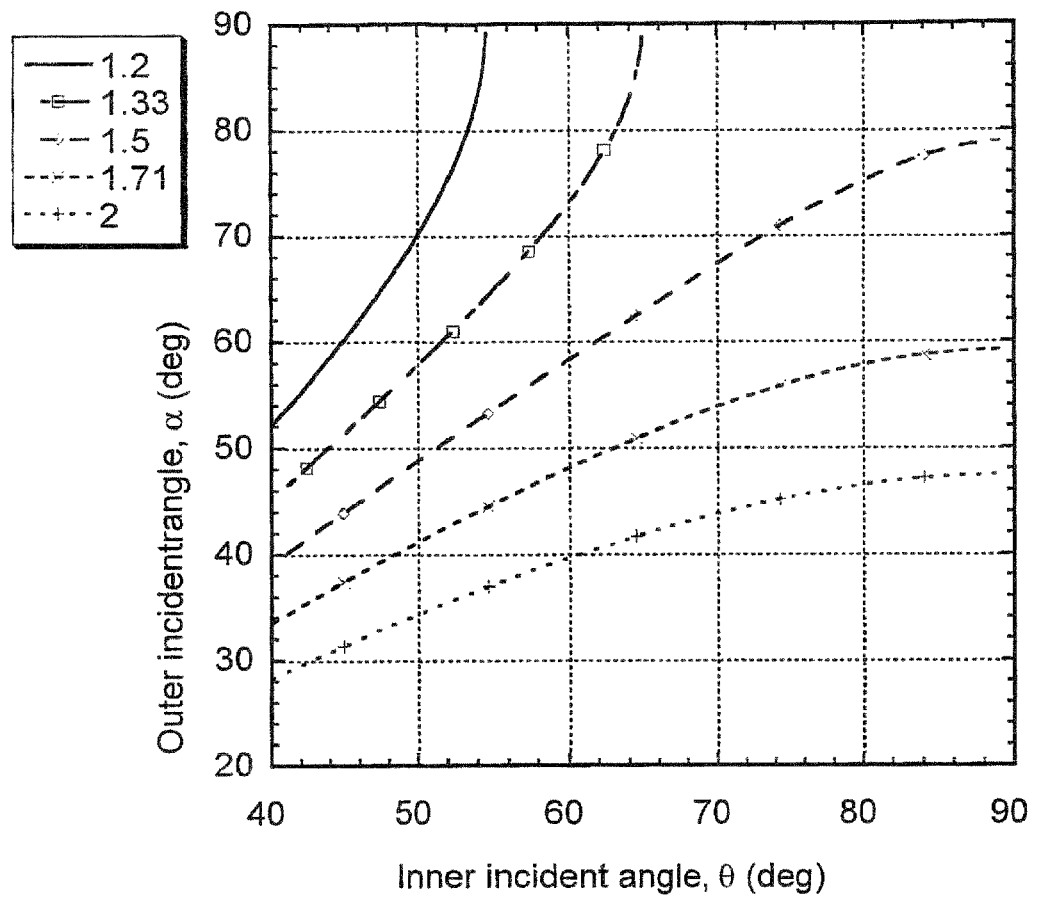
FIG. 16 shows the relation between the outer incident angle (air-glass interface) and the inner incident angle (SPR-angle).

FIG. 16 illustrates the incident angle, $\alpha$, at the outer surface of the substrate 103 as a function of the incident angle, $\theta$, at the inner surface, at different inner and outer radii ratios, 1.2, 1.33, 1.5, 1.71, and 2, for a substrate 103 made of Schott Duran glass in air. If the ratios are greater than the ratio between the refractive indices of the substrate 103 and the ambient, it is not possible to obtain all incident angles, $\theta$, at the inner surface.

Figure 17:
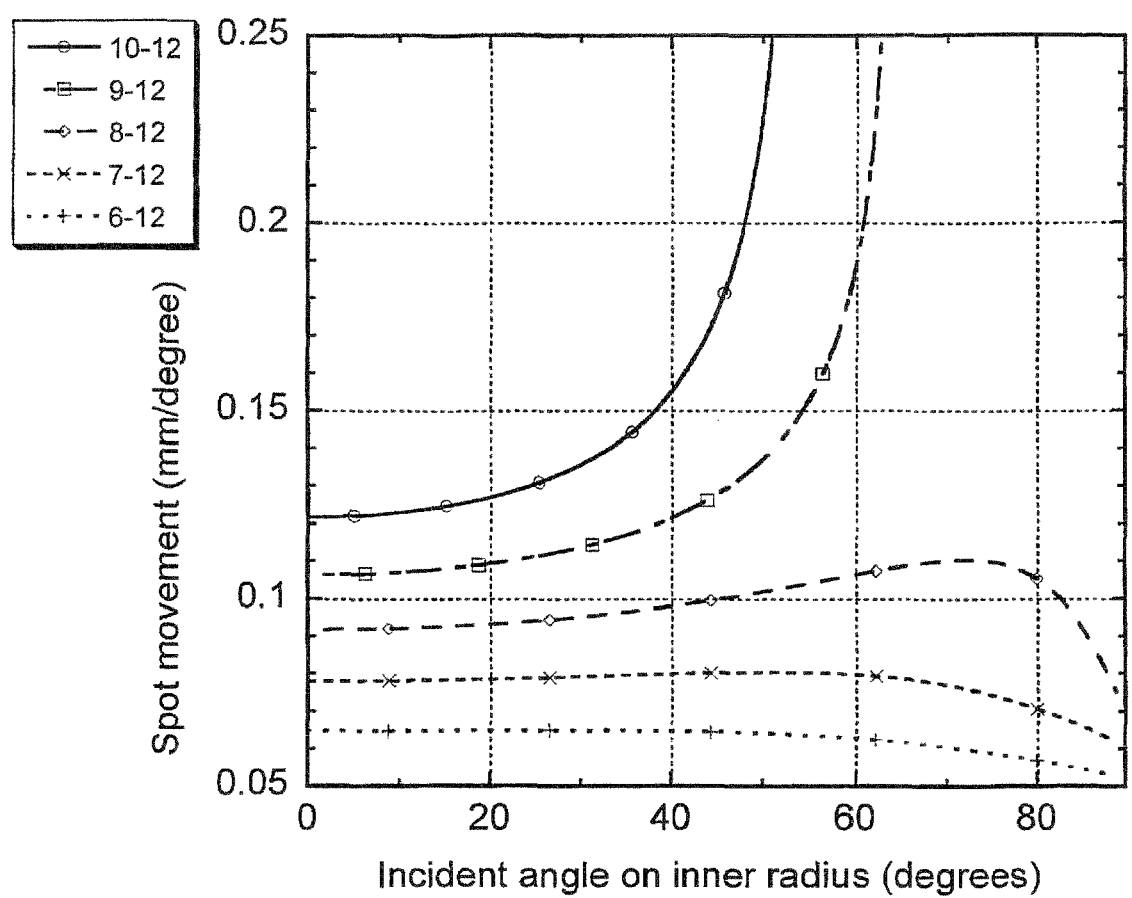
FIG. 17 shows the movement of the spot position (in mm/°) versus the incident angle (SPR-angle) for different inner diameter of the device.
Figure 18:
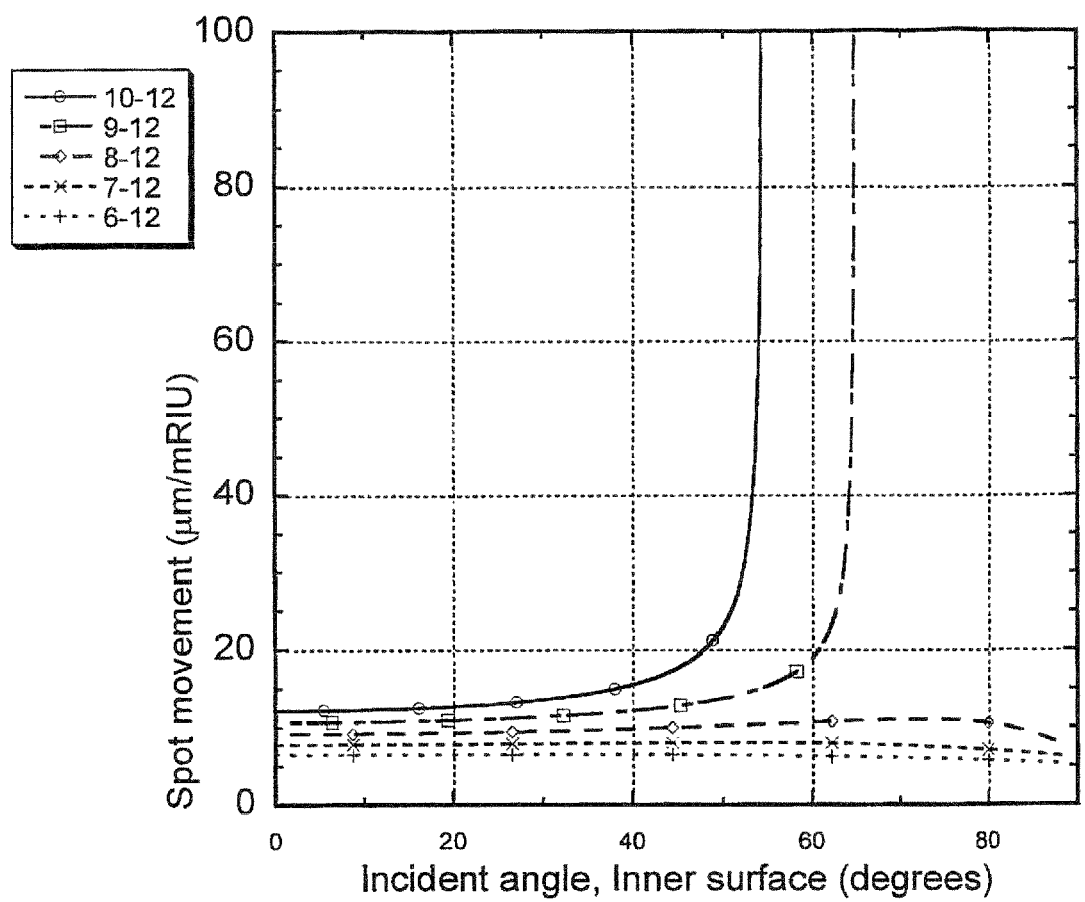
FIG. 18 shows the movement of the spot position (in μm/mRIU) versus the incident angle (SPR-angle) for different inner diameter of the device.

For a collimated input beam 300 with a physical width, there are a diversity of incident angles, $\theta$, along the inner surface of the substrate 103, which means that the resonance angle $\theta_{SP}$ will occur at different places along the inner surface. The movement of the measuring spot as a function of the incident angle (e.g. resonance angle) at the inner surface of the substrate 103 is given in FIG. 17 for different values of the inner diameter, $r_i$, (6, 7, 8, 9, and 10 mm) at an outer diameter of 12 mm of the substrate made of Schott Duran glass. Using the approximation of a change of $10^{-6}$ refractive index units corresponds to $10^{-4}$ degrees in resonance shift of $\theta_{SP}$, leads to a sensing spot movement as illustrated in FIG. 18. The conditions are the same as for FIG. 17.

Propagation Vector Mis-Match

Figure 19:
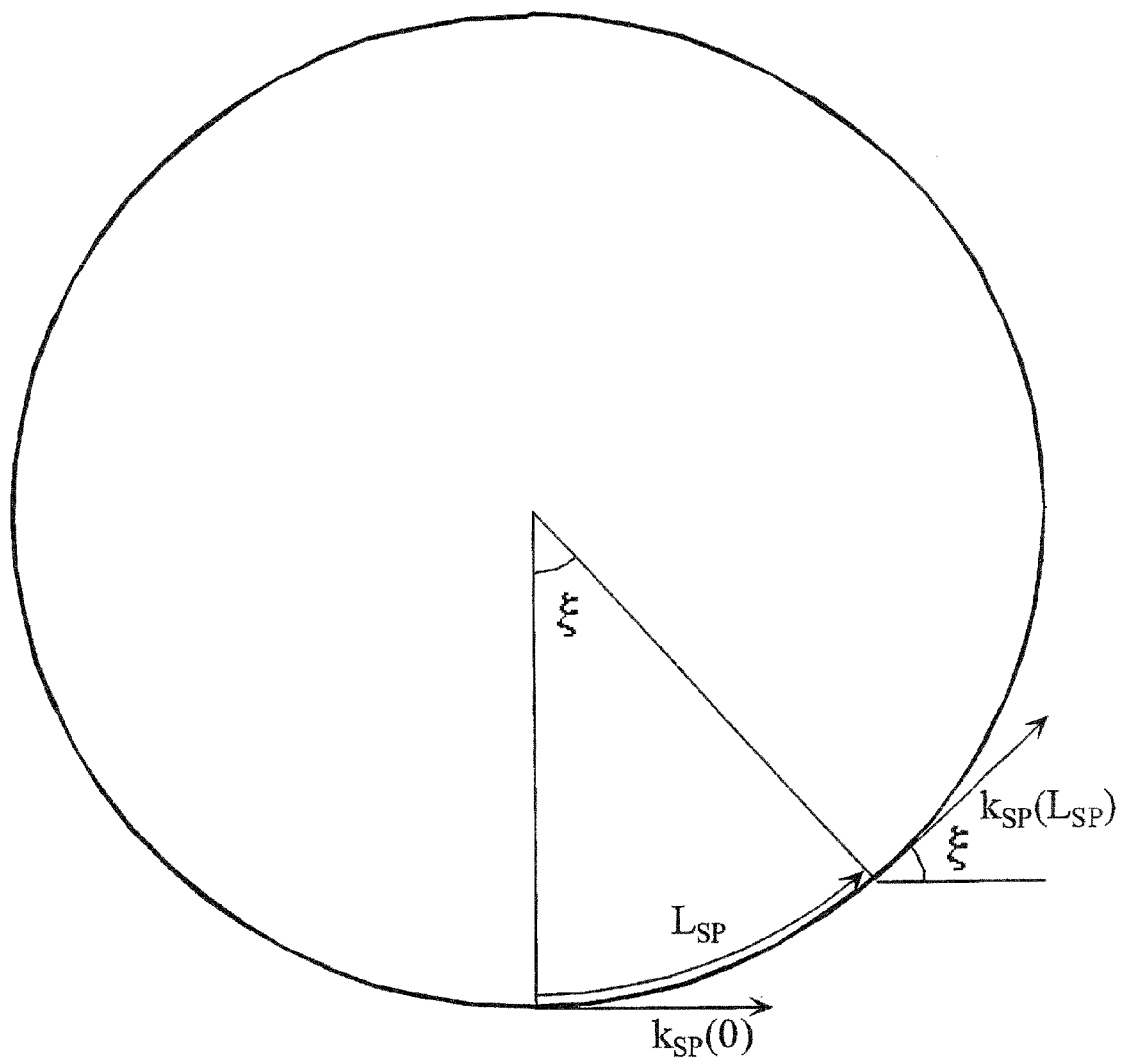
FIG. 19 shows the difference in directions of the surface plasmon propagation vector due to the propagation length and the curvature of the surface of the device

FIG. 19 illustrates the mismatch between the surface plasmon wave vector, $k_{SP}$, and the parallel component of the exciting light at the start $k_{SP}(0)$ and at the propagation length $k_{SP}(L_{SP})$ of the surface plasmon, due to the curvature of the substrate 103. The angular mismatch (in radians) at the characteristic propagation length is given by $\xi$. Where $\xi$ is given by the formula:

$$\xi = \frac{L_{SP}}{r_i} \tag{11}$$

Closed Cavity

Figure 20A:
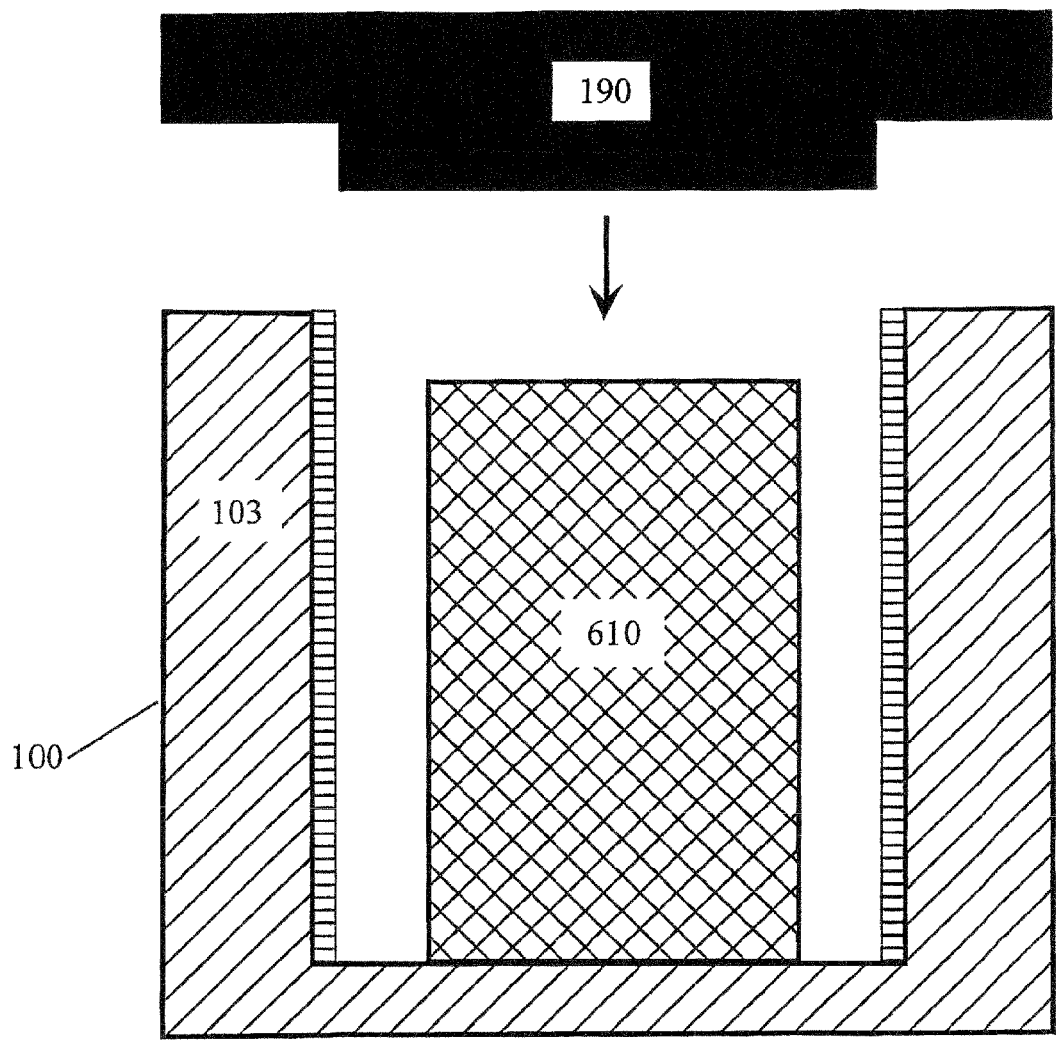
FIG. 20a-c show the device with a cap or two caps.
Figure 20B:
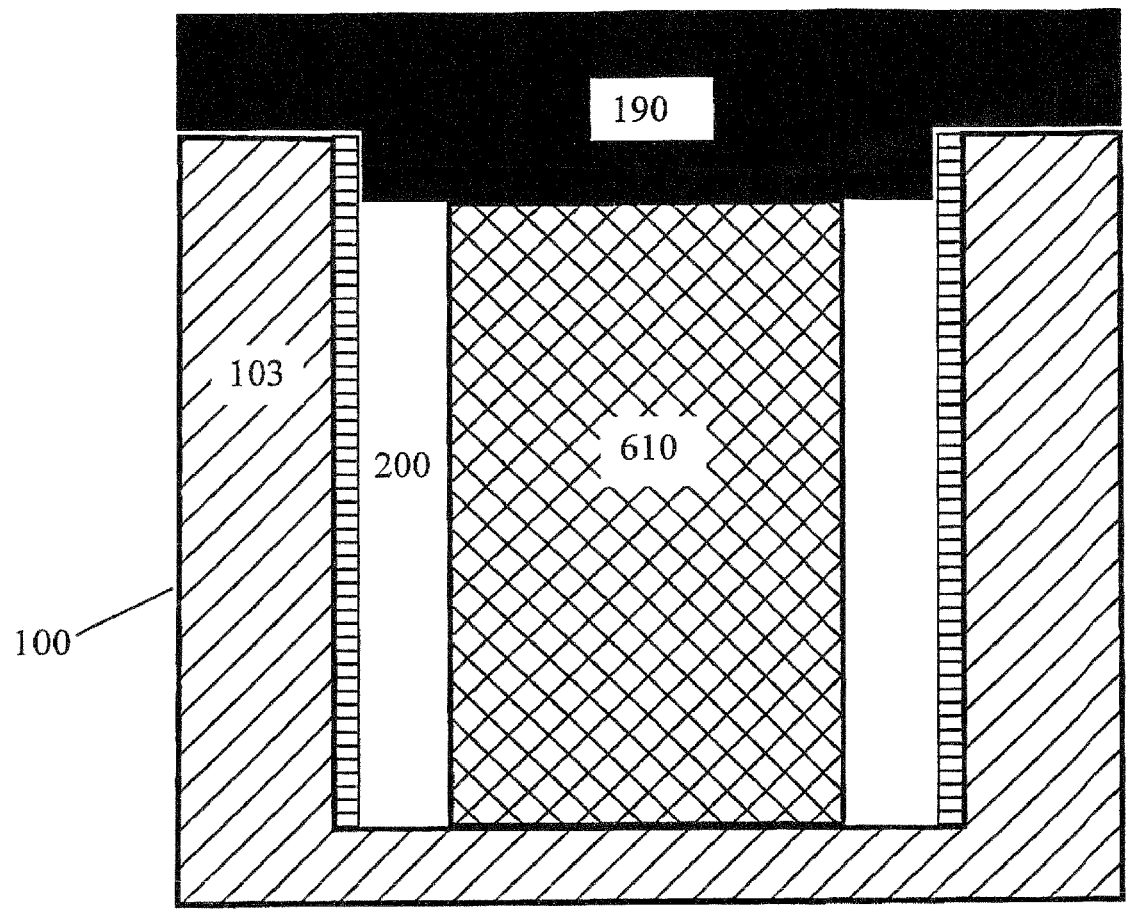
Figure 20C:
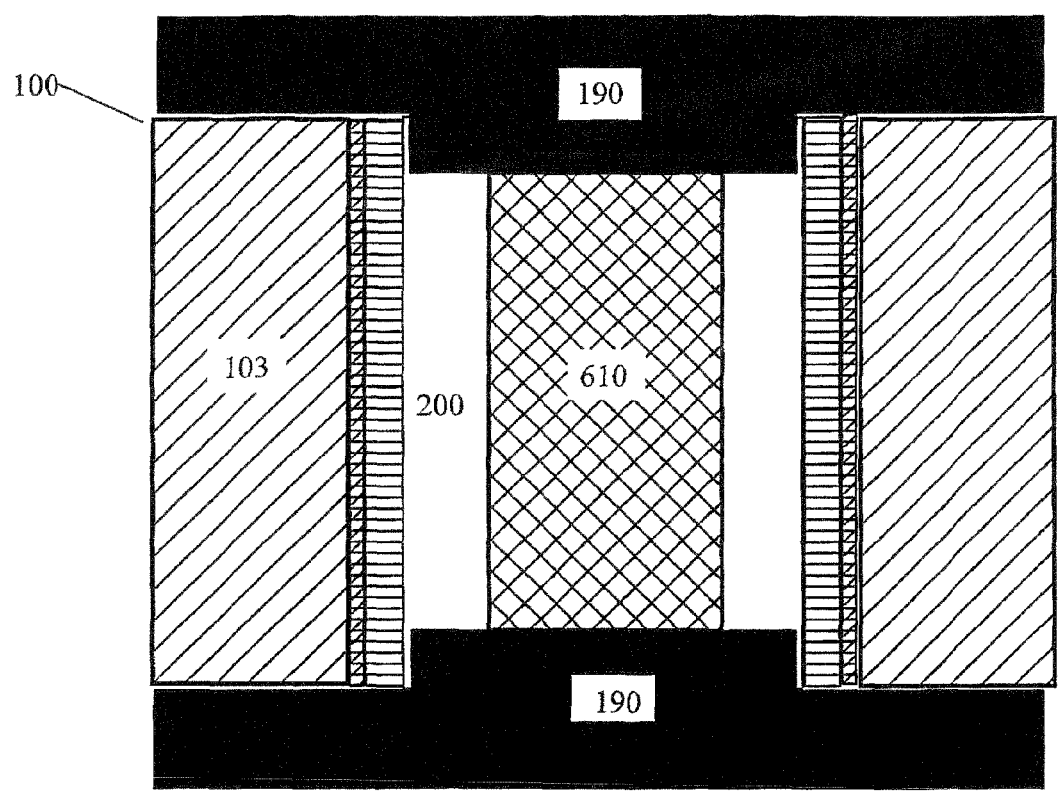

FIG. 20a-c illustrates how the sensor unit 100 can be closed in one or both ends by means of a cap 190.

Figure 21:
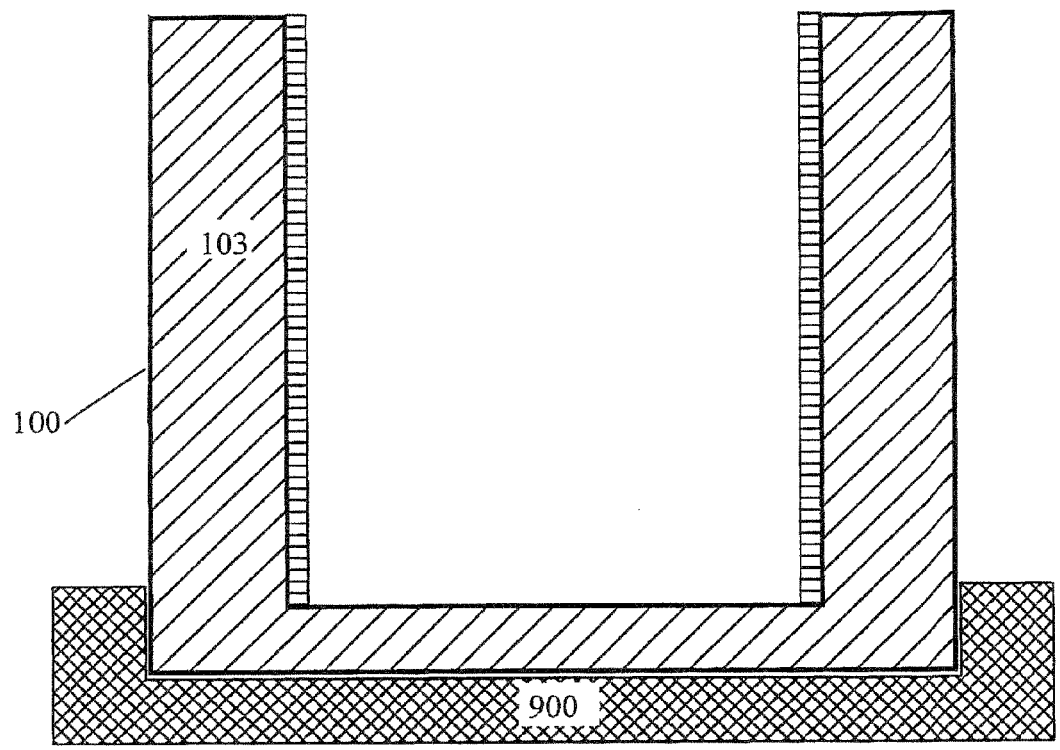
FIG. 21 shows the device placed in a holder.

FIG. 21 illustrates a sensor unit 110 placed in a holder 900 ensuring exact positions.

Example 1

Experiments

Figure 22A:
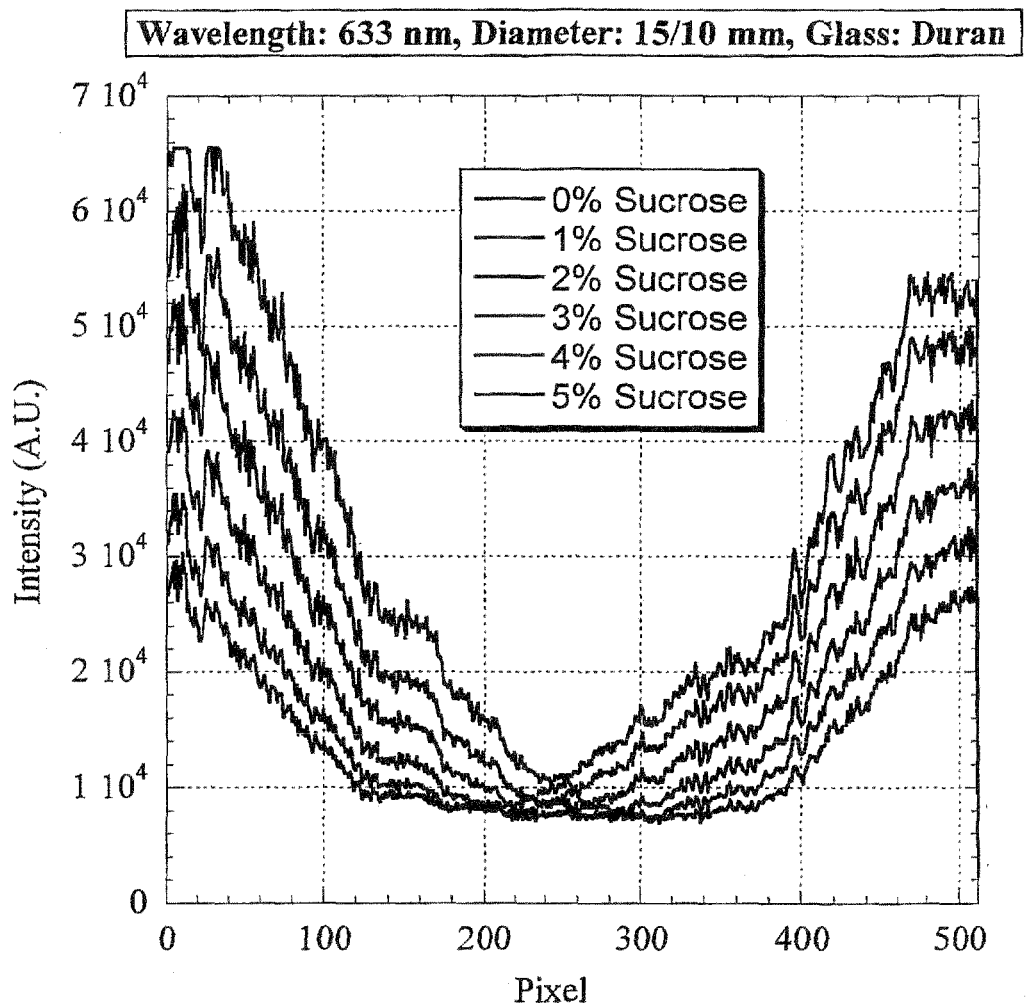
FIG. 22a-b, illustrates the detector signal from experiments using the apparatus with different refractive indices of the sample.

FIG. 22a, illustrates the signal from the detector 500, seen on the computer 800 from one embodiment of the surface plasmon resonance apparatus of the invention as illustrated in FIG. 3a-b. The embodiment utilizes a monochromatic light source comprising a 5 mW HeNe laser (Melles-Griot) 400, emitting coherent and p-polarized (with respect to the sensor surface) light 300 at a wavelength of 633 nm. The light 300 impinges on the outer surface of the substrate 103 made of Duran (Schott) glass with a refractive index of 1.5, and with outer and inner diameters of 15 mm and 10 mm respectively. The glass substrate is sputtered with approximately 0.5 nm chromium acting as the adhesion layer 105 for the surface plasmon supporting metal layer 110. The surface plasmon supporting metal layer 110 is sputtered to a thickness of 50 nm. Both metal layers 105 and 110 are deposited using physical vapor deposition techniques (PVD). Sample 200 consists of sucrose solutions ranging from zero to 5% w/w surcrose in deionized water (Millipore) in steps of 1%. The sucrose solutions 200 get the following refractive indices: 1.3330, 1.3337, 1.3359, 1.3379, 1.3388, and 1.3403. The reflected light pattern 330 from the sensor surface impinges on the CCD camera 500 (Orbis 2, Spectra Source Inc.). The computer 800 is an ordinary PC.

Figure 22B:
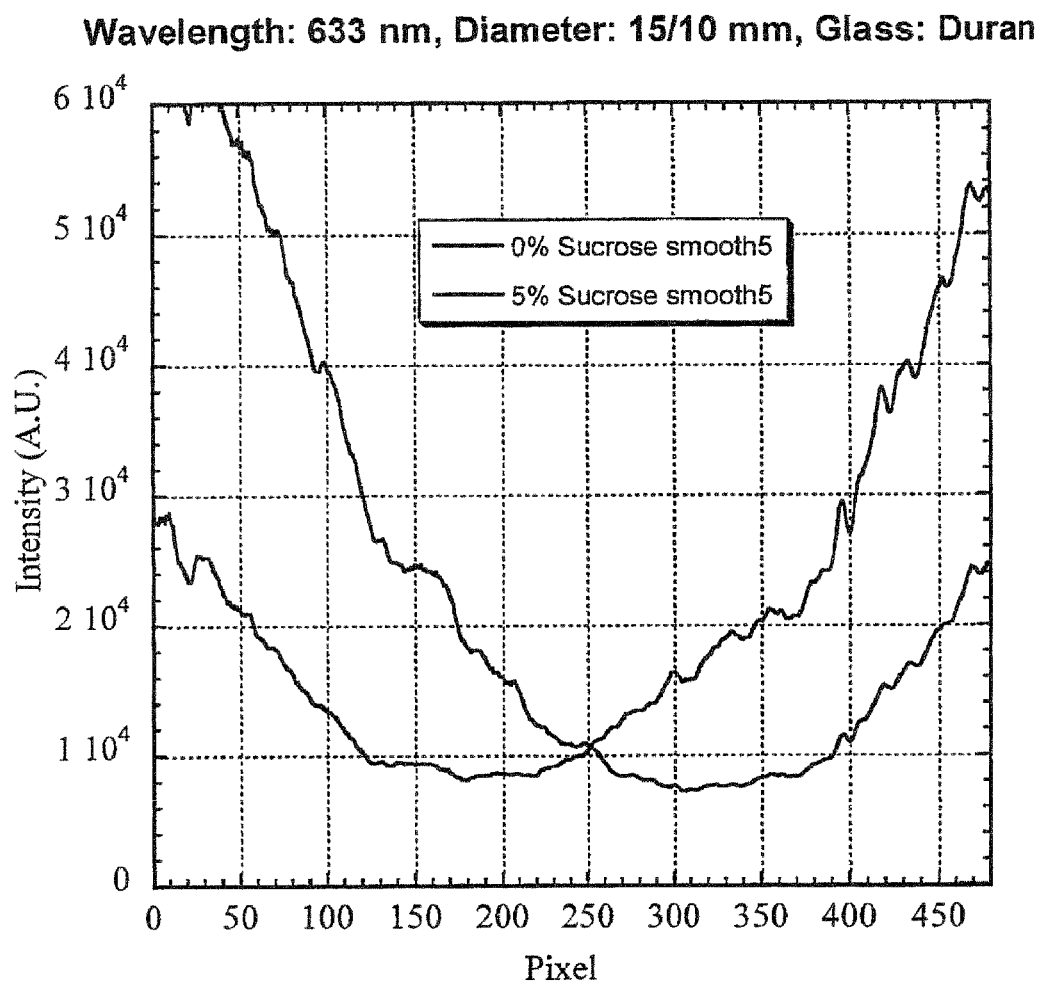

FIG. 22b, illustrates the signal from the detector 500, with noise reduction by the computer 800 for two refractive indices (1.33 and 1.34) of the sample 200.

Figure 23A:
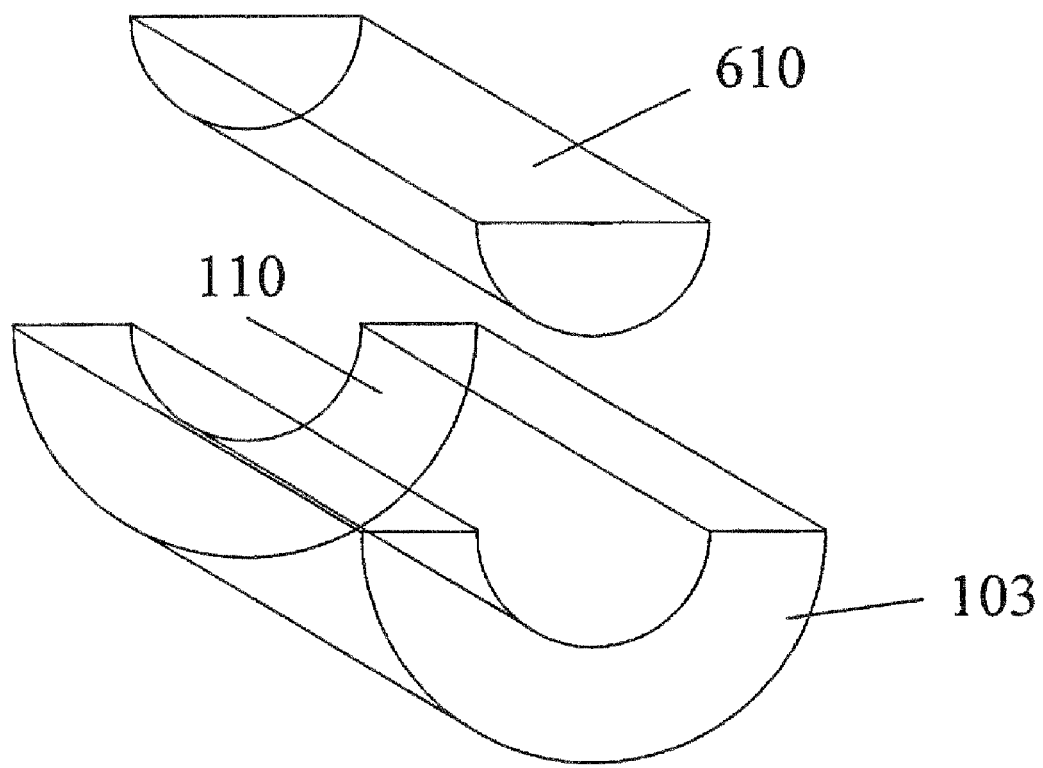
FIG. 23a, illustrates exploded view of the sensor unit as an angular cut out, here as a half pipe with a flow insert.

FIG. 23a, illustrates an exploded view of the sensor unit 100 as an "angular cut out" of the substrate 103, here as a half pipe. At least one, but not limited to one, insert 610 is placed in the cavity, either in direct contact with the surface using flow channels in the insert 610, or in the vicinity of the surface with or without a structure to control the flow of gas or fluid used. The use of an "angular cut" substrate means that formation of the adhesion layer 105 as shown in FIG. 5 and conductive layer 110 is easily formed by traditional physical vapor deposition (PVD) techniques, such as evaporation, electronic beam, and sputtering. Moreover, angular break up of the structure means that there will be an open large cavity which will help formation of the molecular recognition layers 130 as shown in FIG. 6, with a plurality of techniques, as soft lithography stamps etc.

Figure 23B:
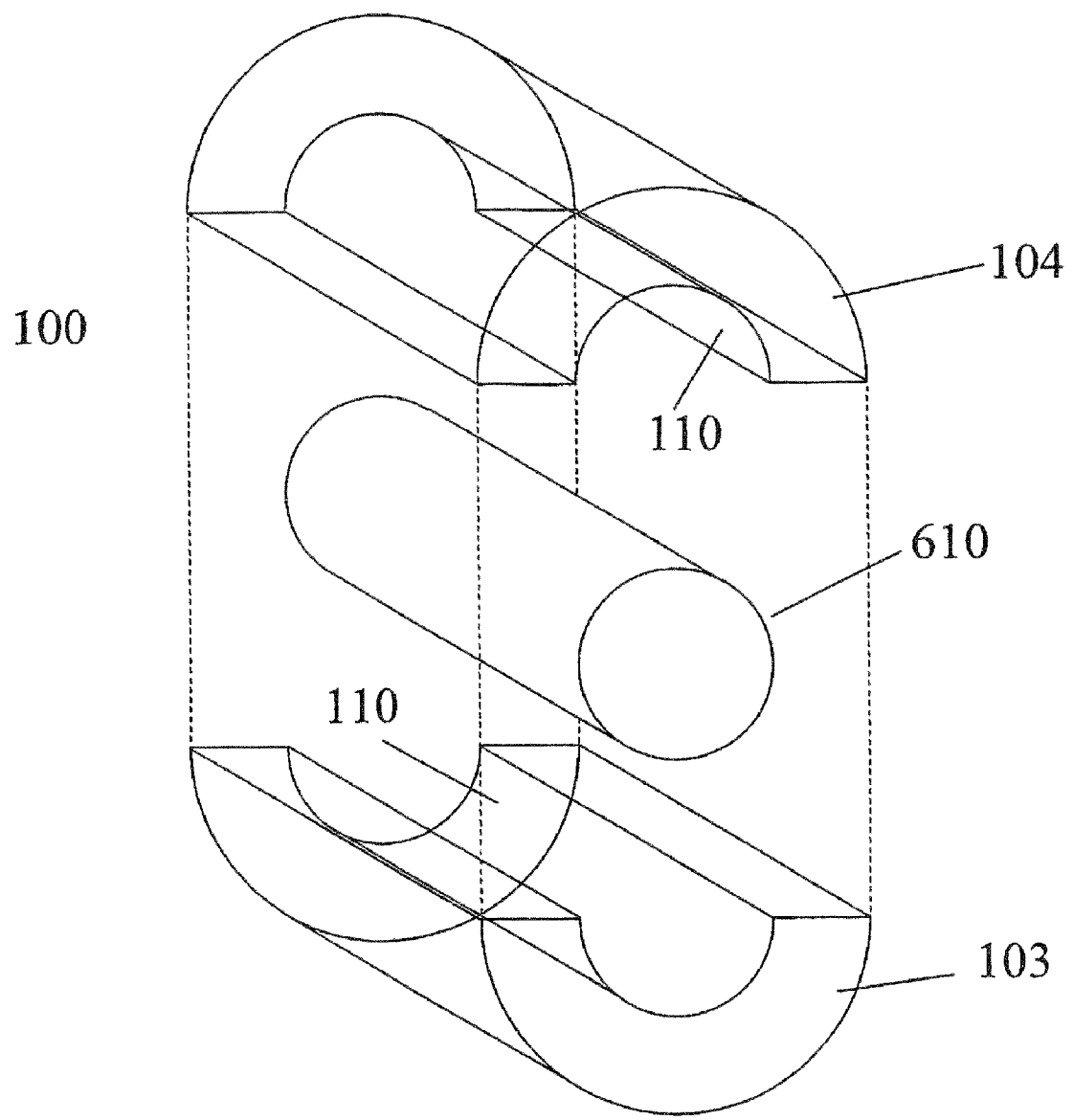
FIG. 23b, illustrates an exploded view the sensor unit built from two or more elements, with a flow insert.

FIG. 23b, illustrates an exploded view of the sensor unit 100 as assembled of two, but not limited to that number, substrates 103 and 104 forming a large cavity, in which a flow controlling part 610 is inserted, either in contact with the inner surface or in the vicinity. The flow controlling part has preferably integrated flow channels when in contact with the curved surface. The setup is not limited to that for the case when the insert 610 is in contact with the surface. For the non contacting case the insert 610 will preferably rotate or oscillate in the large cavity formed by the substrates 103 and 104, or vice versa when the substrates 103 and 104 together are moving, or both when both insert 610 and both substrates 103 and 104 is moving.

Figure 24:
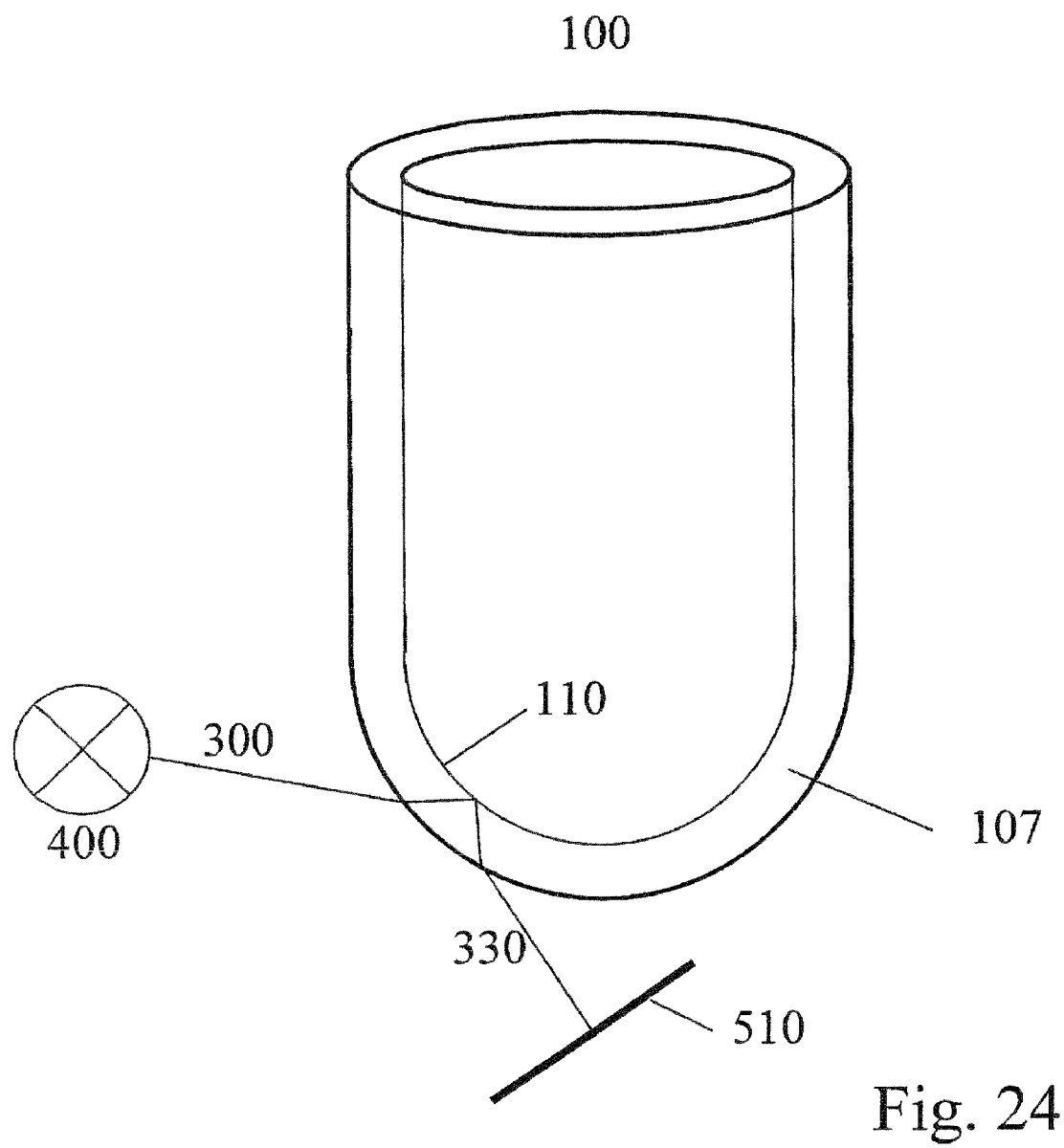
FIG. 24, illustrates a sensor unit where at least one sensor surface is double curved.

FIG. 24, illustrates a sensor unit 100 with a double curved surface 107, e.g. the bottom of a vial, with a surface plasmon supporting conductive layer 110, where the surface plasmon can be excited in many directions.

Figure 25:
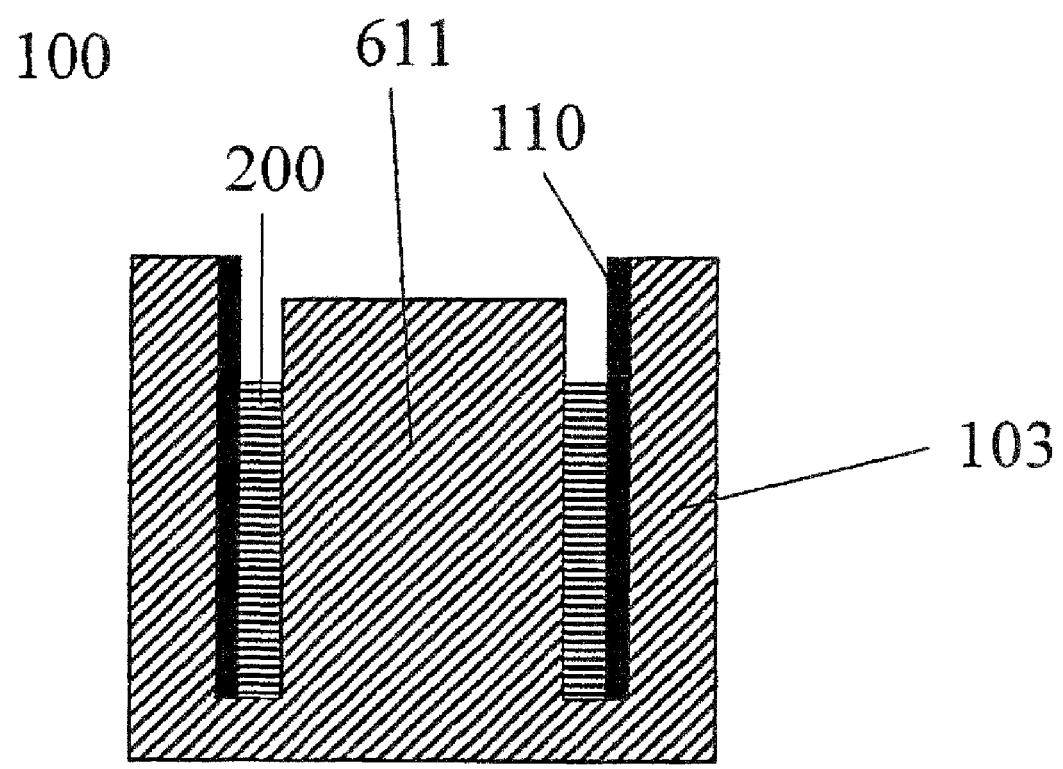
FIG. 25, illustrates a cross section of a rotational symmetric sensor unit with an integrating flow structure

FIG. 25, illustrates a sensor unit 100 with an integrated flow structure 611 into the optical substrate 103. The cavity that is formed between the substrate 103 and the flow structure 611 is filled with a sample 200. The surface plasmon supporting conductive layer 110 is present at the concave surface of the wall.

Figure 26A:
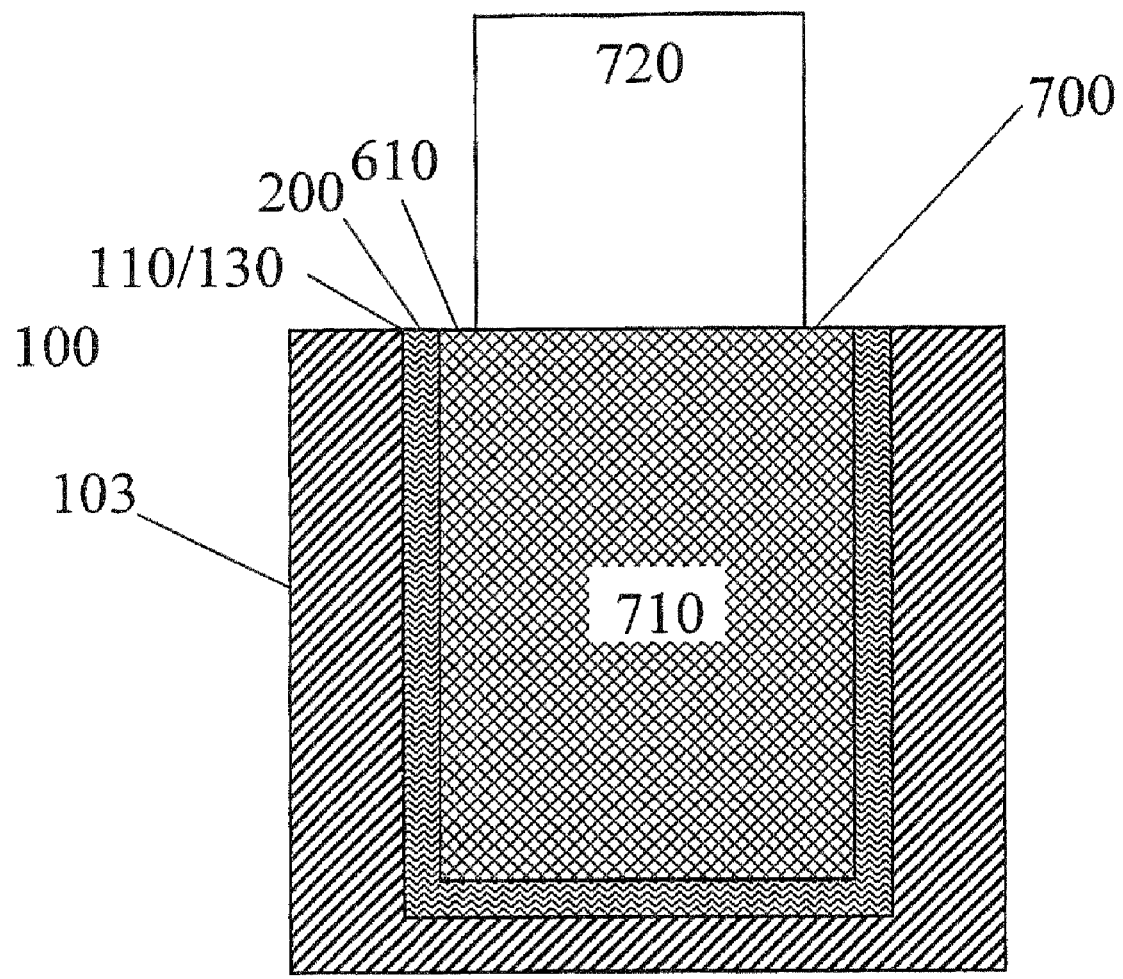
FIG. 26a, illustrates an embodiment with thermo controlled sensor unit.

FIG. 26a, illustrates a sensor unit 100 with a flow structure 610 inserted in the optical substrate 103. The cavity that is formed between the substrate 103 and the flow structure 610 is filled with a sample 200. The molecular recognition sites 130 are placed on the surface plasmon supporting conductive layer 110 which is present at the concave surface of the wall of the substrate 103. The flow structure incorporates a temperature control unit 700 the purpose of which is to keep sample at sensor surface at a controlled temperature. Temperature can either be held constant or ramped. The thermo control unit consists basically of two parts, one sample temperature unit 710 which performs the local heat exchange at the sensor surface, and a heat/cold supplying unit 720, which supplies the sample temperature unit with heat or cold. The sample temperature unit 710 is in a simple embodiment, typically a piece of metal, and in a more advanced embodiment an insert made of e.g. polymers, ceramics, metal or a combination of these materials with channels for liquids carrying the heat flux. The heat/cold supplying unit is typical a thermoelectrical device (e.g. Peltier unit), but can also be a conventional compressor with heater/condenser or for the case only heating is necessary, a resistive element. Using a resistive element, the unit can be integrated with the sample temperature unit 710, forming a single unit. To obtain fast temperature ramps, different temperatures can be provided simultaneously at the heat/cold supplying unit 720, and these temperature stores can be switched into the sample control unit 710.

Figure 26B:
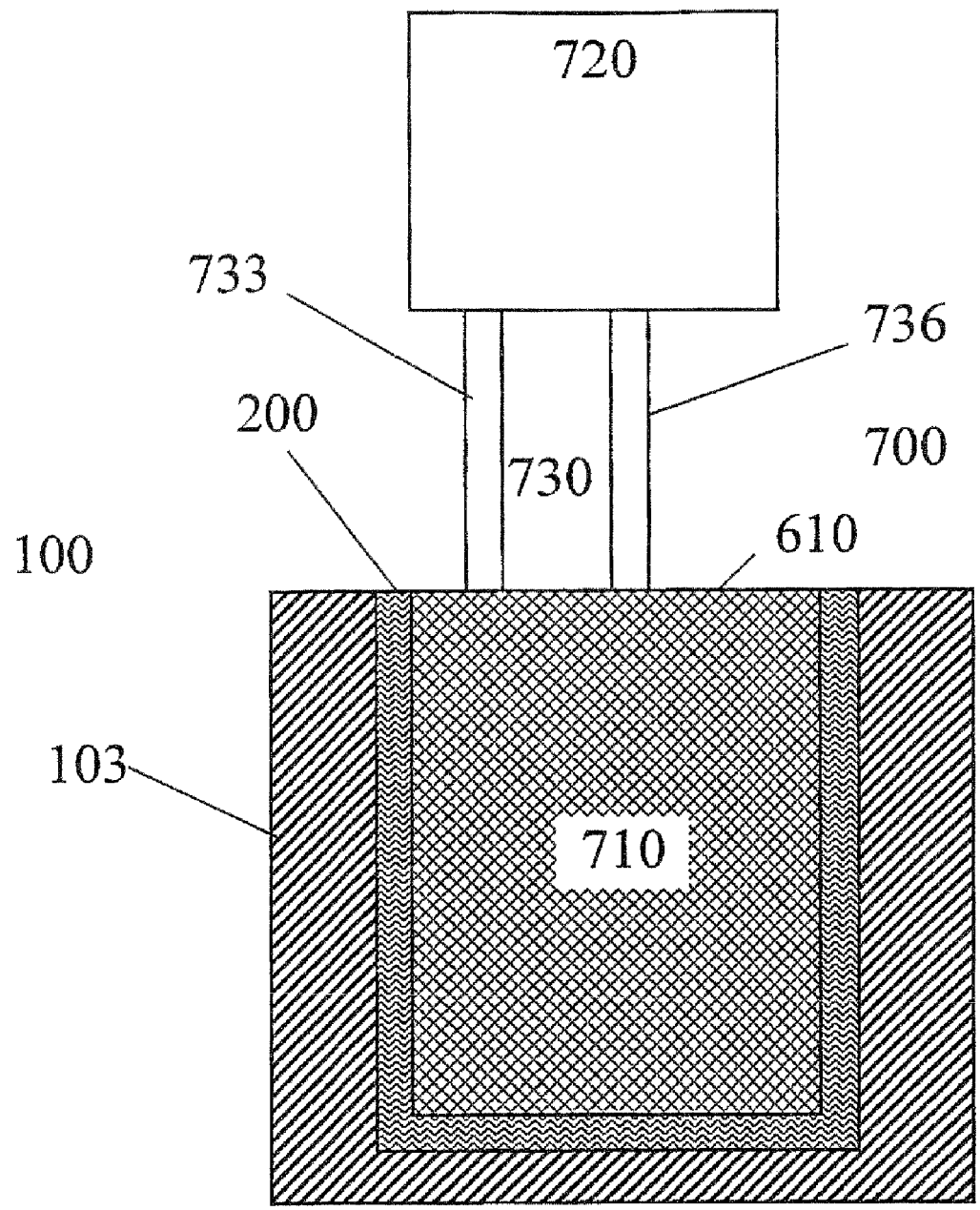
FIG. 26b, illustrates an embodiment where the thermal flux is directed to the sensor unit by tubes.

FIG. 26b, illustrates a temperature control unit 700, where the sample temperature unit 710 and heat/cold supply unit 720 is separated by tubes, inlet 733 and outlet 736 carrying the liquid for thermal control.

Figure 26C:
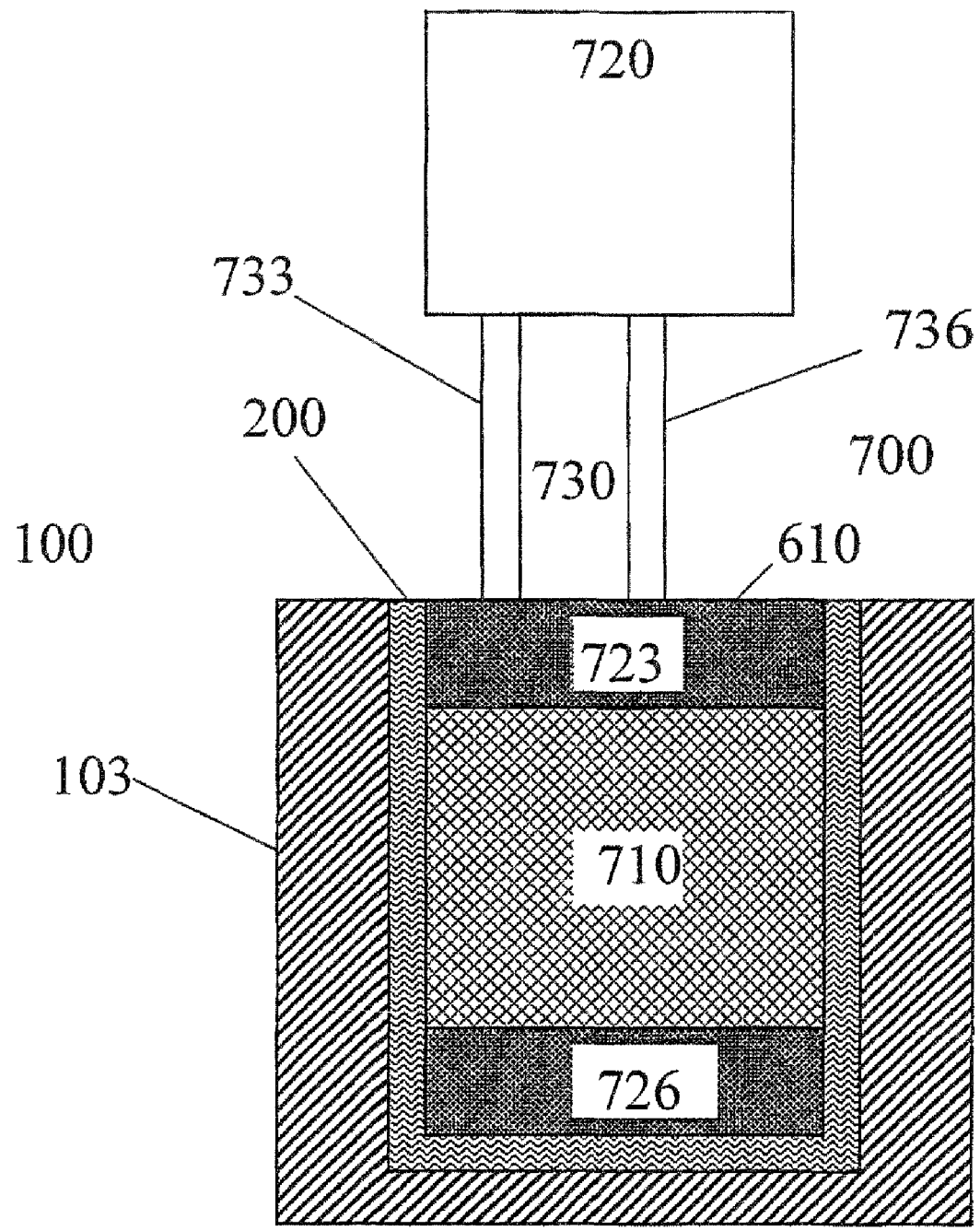
FIG. 26c, illustrates an embodiment where there are different temperatures on different places on the sensor unit, creating a temperature gradient.

FIG. 26c, illustrates a temperature control unit 700, where the sample temperature unit 710 has two (or more) separated temperature zones 723 and 726, creating a temperature gradient between them.

Figure 27:
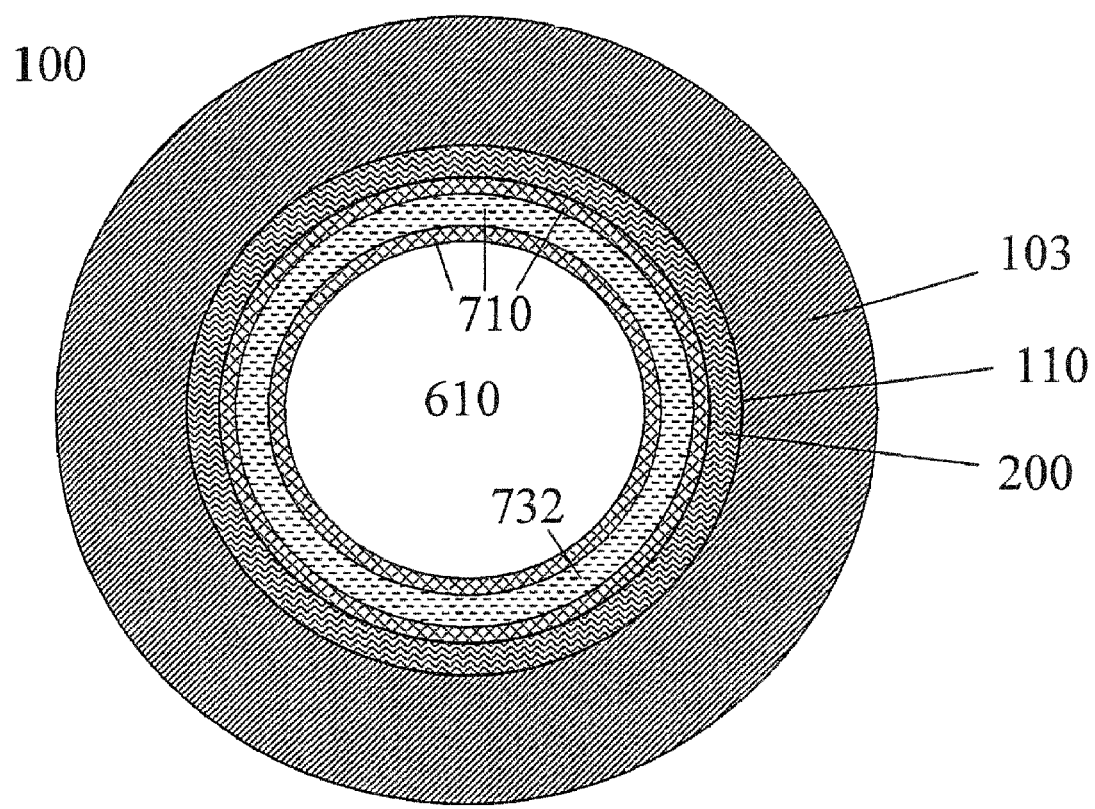
FIG. 27, illustrates an embodiment where heat flux is transferred by a liquid close to the sensor surface.

FIG. 27a, shows the sample temperature unit 710 inserted into the substrate 103, with the temperature controlling liquid 732 close to the sample 200, therefore obtaining fast and precise temperature control of the sample.

Typical fixed temperatures are 25 and 37 degrees centigrade.

Figure 28:
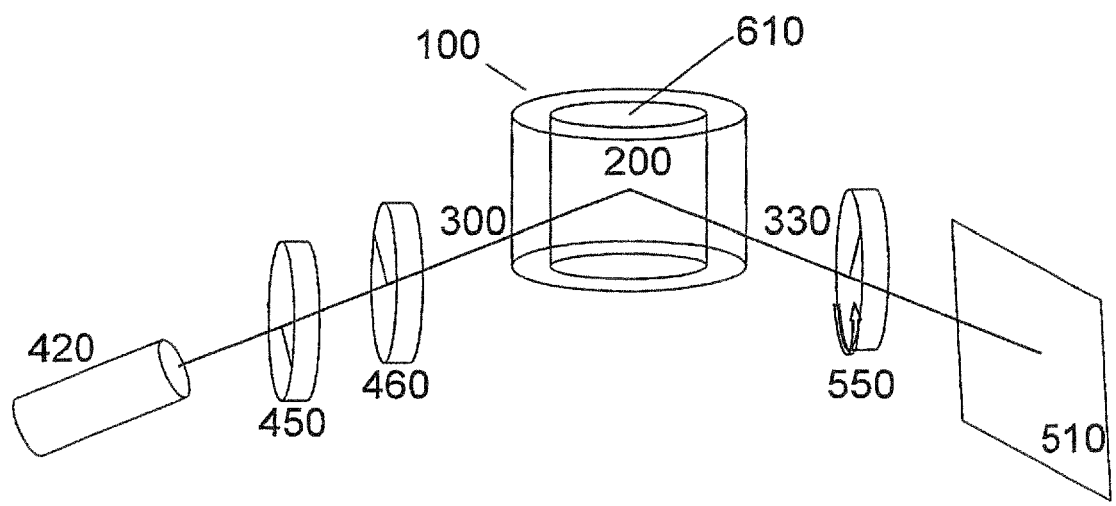
FIG. 28, illustrates an embodiment for measurement of the polarization state.

FIG. 28, shows an ellipsomeric setup, i.e. measurement of the polarisation state. The light source 420, which can be monochromatic or multispectral, provides both p- and s-polarized light. This basic setup can be used for compensated as well as uncompensated ellipsometry. The uncompensated ellipsometer is shown as a PCSA-setup. For this case the compensator 460, which is a quarter wave plate, is set to 45° to introduce a phase shift between the p- and s-polarized light. Both the polarizer 450 and analyzer 550 are rotated until the light at the detector 510 vanishes. The setup can also be used off-null, where both the analyzer 550 and polariser 450 are fixed at azimuths close to zero light at the detector 510. A rotating analyser ellipsometer, RAE, is obtained for a fixed polarizer 450, usually at 45°, and a rotating analyzer 550. For this case the compensator 460 is optional. The light source 410 and detector 510 can be used in imaging.

REFERENCES

1. Nylander, C., B. Liedberg, and T. Lind, *Gas Detection by Means of Surface Plasmon Resonance*, Sensors and Actuators, 1983. p. 79-88.
2. Abdelghani, A., et al., *Surface Plasmon Resonance Fiber-Optic Sensor for Gas Detection*. Sensors and Actuators B-Chemical, 1997. B38-39: p. 407-410.
3. Tengvall, P. and I. Lundström, *Determination of polymerization/coagulation in a fluid*. 1998, GLOBAL HEMOSTASIS INST MGR AB (SE); TENGVALL PENTTI (SE); LUNDSTROEM INGEMAR (SE).
4. Vikinge, T. P., et al. *Blood plasma coagulation studied by surface plasmon resonance*. in Bios '98. 1998. Stockholm.
5. Hansson, K. M., et al., *Surface Plasmon Resonance (SPR) Analysis of Coagulation in Whole Blood with Application in Prothrombin Time Assay*. Biosensors & Bioelectronics, 1999. 14: p. 671-682.

6. Vikinge, T. P., et al., *Blood Plasma Coagulation Studied by Surface Plasmon Resonance*. Journal of Biomedical Optics, 2000. 5: p. 51-55.
7. Kretschmann, E. and H. Raether, *Radiative Decay of Non Radiative Surface Plasmon Excited by Light*. Zeitschrift für Naturforschung, 1968. 23 A: p. 2135-2136.
8. Sjölander, S., et al., *Optical biosensor system*. 1988, Pharmacia Biosensor AB.
9. Melendez, J., et al., *A Commercial Solution for Surface Plasmon Sensing*. Sensors and Actuators B-Chemical, 1996. 35-36: p. 212-216.
10. Karlsen, S. R., et al., *First-order surface plasmon resonance sensor system based on a planar light pipe*. Sensors and Actuators B-Chemical, 1996. 32: p. 137-141.
11. Chinowsky, T. M. and S. S. Yee, *Surface Plasmon Resonance Sensing in Capillaries*. Electronics Letters, 1999. 35(19): p. 1659-1661.
12. Jorgenson, R. C., et al. *Surface Plasmon Resonance fiber optic biosensors*. in *Europtrode 2*. 1994.
13. Jorgenson, R. C., et al. *Surface Plasmon Resonance fiber optic sensor long-term stability and robustness studies*. in *Europtrode 2*. 1994.
14. Jorgenson, R. C., U.S. patent, Fiber Optic Sensor and Methods and apparatus relating thereto, in U.S. Pat. No. 5,359,681, S. S. Yee, Editor. 1994: USA.
15. Turbadar, T., *Complete Adsorption of Light by Thin Metal Films*. Proc. Phys. Soc. Lond., 1959. 73: p. 40-44.
16. Otto, A., *Excitation of Nonradiative Surface Plasma Waves In Silver by the Method of Frustrated Total Reflection*. Z. Physik, 1968. 216: p. 398-410.
17. Kretschmann, E., *Die Bestimmung Optischer Konstanten von Metallen Durch Anregung von Oberflächenplasmaschwingungen*. Z. Physik, 1971. 241: p. 313-324.
18. Yeatman, E. and E. Ash, *Surface Plasmon Microscopy*. Electronics Letters, 1987. 23(20): p. 1091-1092.
19. Yeatman, E. M. and E. A. Ash, *Surface plasmon scanning microscopy*. Proceedings of SPIE, 1988. 897 (Scanning Microscopy Technologies and Applications. Symposium date: 13-15 Jan. 1988): p. 100-107.
20. Jordan, C. E. and R. M. Corn, *Surface Plasmon Resonance Imaging Measurements of Electrostatic Biopolymer Adsorption onto Chemically Modified Gold Surfaces*. Analytical Chemistry, 1997. 69(7): p. 1449-1456.
21. Jordan, C. E., et al., *Surface Plasmon Resonance Imaging Measurements of DNA Hybridization Adsorption and Streptavidin/DNA Multilayer Formation at Chemically Modified Gold Surfaces*. Analytical Chemistry, 1997. 69(24): p. 4939-4947.
22. Rothenhäusler, B. and W. Knoll, *Surface-plasmon microscopy*. Nature, 1988. 332: p. 615-617.
23. Hickel, W., B. Rothenhäusler, and W. Knoll, *Surface plasmon microscopic characterization of external surfaces*. Journal of Applied Physics, 1989. 66(10): p. 4832-4836.
24. Rothenhäusler, B. and W. Knoll, *Interferometric determination of the complex wave vector of plasmon surface polaritons*. Journal of Optical Society of America B, 1988. 5(7): p. 1401-1405.
25. Fernandez, U., T. M. Fischer, and W. Knoll, *Surface-plasmon microscopy with grating couplers*. Optics Communications, 1993. 102: p. 49-52.
26. Raether, H., *Surface Plasmon on Smooth and Rough Surfaces and on Gratings*. Springer Tracts in Modern Physics, ed. G. Höhler. 1988, Heidelberg: Springer-Verlag.

The invention claimed is:

1. A sensor unit for a Surface Plasmon Resonance (SPR) unit, comprising:
   a) a transparent sensor structure forming at least one wall of a cavity, the wall being defined by a concave inner surface and a convex outer surface; wherein
   b) the inner surface is provided with a layer of a conductive material capable of supporting a surface plasmon;
   c) a flow structure in said cavity so as to form at least one compartment for sample between the flow structure and the inner wall of the cavity.

2. The unit according to claim 1, wherein the ratio between the radii of said concave inner and convex outer surfaces are defined so that an incident angle at said inner concave surface in said wall is close to or greater than a critical angle, and incorporating the angles around the resonance angle for said surface plasmon where there are a significant reduction in reflectance of light.

3. The unit according to claim 1, wherein the cavity is defined by one of a tube, a vial, a longitudinal cut pipe, a half-pipe, and a cup.

4. The unit according to claim 1, wherein said sensor unit is one of a closed structure, a cup having a bottom, a closed vial, a cup, and container.

5. The unit according to claim 1, wherein curvatures have different radii at different positions along the longitudinal axis.

6. The unit according to claim 1, wherein the cavity has one of a conical shape, and part of a conical shape.

7. The unit according to claim 1, wherein said inner surface layer of conductive material is covered with at least one of a specific and non-specific area comprising at least one of an adsorption and reaction layer/layers for at least one of molecules and atoms.

8. The unit according to claim 1, wherein said flow structure incorporates one or a plurality of flowcells in radial, axial or arbitrary directions compared to said longitudinal axis of said sensor unit.

9. The unit according to claim 1, wherein said flow structure is a bob, which is fixed, rotatable, or can be set in oscillation.

10. The unit according to claim 9, wherein the distance between said bob and said concave inner surface varies along said longitudinal axis, so as to create different shear rates for fluids when the bob and the sensor structure have different angular velocities.

11. The unit according to claim 1, wherein said cavity incorporates a waste.

12. The unit according to claim 1, wherein said flow structure incorporates a sample temperature unit which controls a temperature of the sample.

13. The unit according to claim 1, wherein a sample temperature unit creates a temperature gradient of the sample.

* * * * *